United States Patent [19]

Ueda et al.

[11] Patent Number: 4,730,051
[45] Date of Patent: Mar. 8, 1988

[54] 4-(SUBSTITUTED-OXY)-3-PYRIDINECARBOXAMIDES USEFUL AS PLANT GROWTH INHIBITORY AGENTS

[75] Inventors: Yoichiro Ueda; Yukihisa Goto; Kazuhisa Masamoto, all of Himeji; Yoshiyuki Hirako, Otake; Hiroshi Yagihara, Himeji; Yasuo Morishima, Kobe; Hirokazu Osabe, Himeji, all of Japan

[73] Assignee: Daicel Chemical Industries Ltd., Osaka, Japan

[21] Appl. No.: 819,144

[22] Filed: Jan. 15, 1986

[30] Foreign Application Priority Data

Jan. 18, 1985 [JP] Japan .................................. 60-7665
Aug. 2, 1985 [JP] Japan .................................. 60-171673
Sep. 25, 1985 [JP] Japan .................................. 60-211821

[51] Int. Cl.$^4$ .................... C07D 213/56; A01N 43/40
[52] U.S. Cl. .................................. 546/291; 546/316; 546/323; 546/169; 71/94
[58] Field of Search ............... 546/316, 291; 71/84

[56] References Cited

U.S. PATENT DOCUMENTS 3,535,328 10/1970 Zielinski ........................ 546/300
4,566,899 1/1986 Ambrosi et al. .................. 71/93

FOREIGN PATENT DOCUMENTS 1115278 12/1981 Canada ........................... 546/291

Primary Examiner—Alan L. Rotman
Attorney, Agent, or Firm—Stiefel, Gross, Kurland & Pavane

[57] ABSTRACT

A compounds of the general formula (I):

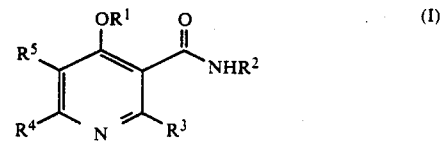

wherein $R^1$ is alkyl, lower alkenyl, lower alkynyl, aralkyl, haloalkyl, lower alkoxy-lower alkyl, lower alkylthio-lower alkyl or lower alkoxycarbonyl-lower alkyl group; $R^2$ is aryl group which may be substituted by one or more groups of halogen atom, lower alkyl, lower alkoxy, lower alkoxycarbonyl, trifluoromethyl, cyano and nitro group; $R^3$ and $R^4$ are, the same or different, lower alkyl, aralkyl, haloalkyl or cycloalkyl, or aryl group which may be substituted by one or more groups of halogen atom, lower alkyl, lower alkoxy, trifluoromethyl, cyano or nitro group; $R^5$ is hydrogen atom, halogen atom, lower alkyl, phenyl which may be substituted or aralkyl which may be substituted; or $R^4$ and $R^5$ may be combined to form a group of —$(CH_2)_n$— in which n is 3 or 4, or its 1-oxide or addition salt. which is useful as a plant growth inhibitory agent.

4 Claims, No Drawings

4-(SUBSTITUTED-OXY)-3-PYRIDINECARBOXA-MIDES USEFUL AS PLANT GROWTH INHIBITORY AGENTS

BACKGROUND OF THE INVENTION

1. Field of the Invention

The present invention is concerned with new 4-substituted-oxy-3-pyridinecarboxamide compounds or 1-oxide thereof and their addition salt, which show plant growth inhibitory activity.

2. Description of the Prior Art

As far as the inventors know, there are no reports on 2,6-disubstituted-4-(substituted-oxy)-3-pyridinecarboxamide compounds and 2,6-disubstituted-4-(substituted-oxy)-3-pyridinecarboxamide 1-oxides and their addition salts, as shown by the formula (I) and (I').

SUMMARY OF THE INVENTION

The present invention relates to compounds of the general formula (I) and 1-oxides of the general formula (I'), and their addition salts:

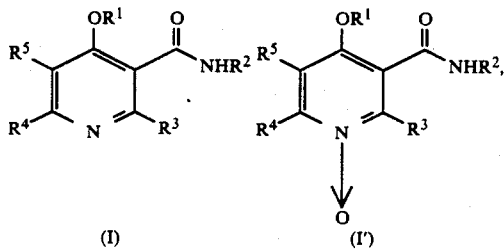

wherein $R^1$ is alkyl, lower alkenyl, lower alkynyl, aralkyl, haloalkyl, lower alkoxy-lower alkyl, lower alkylthio-lower alkyl or lower alkoxycarbonyl-lower alkyl; $R^2$ is an aryl group which may be substituted by one or more groups of halogen atom, lower alkyl, lower alkoxy, lower alkoxycarbonyl, trifluoromethyl, cyano and nitro group; $R^3$ and $R^4$ are, the same or different, lower alkyl, aralkyl, haloalkyl or cycloalkyl, or aryl group which may be substituted by halogen atom, lower alkyl, lower alkoxy, trifluoromethyl, cyano or nitro; $R^5$ is hydrogen atom, halogen atom, lower alkyl, phenyl which may be substituted or aralkyl which may be substituted; or $R^4$ and $R^5$ may be combined to form a group of $-(CH_2)_n-$ (n is 3 or 4).

In this invention, alkyl group includes linear and branched hydrocarbon such as methyl, ethyl, propyl, isopropyl, butyl, isobutyl, pentyl, isopentyl, hexyl or octyl, and also includes cycloalkyl alkyl such as cyclohexylmethyl or cyclopropylmethyl.

The term "lower" used in the invention is intended to mean up to 6 carbon atoms. Specifically, there may be mentioned, as lower alkyl groups, methyl, ethyl, propyl, isopropyl, butyl, isobutyl, tertiary butyl, pentyl or isopentyl; as lower alkenyl and lower alkynyl groups, allyl, 2-methyl-2-propenyl, but-2-enyl, pent-2-enyl or 2-propynyl.

Examples of lower alkoxy-lower alkyl and lower alkylthio-lower alkyl groups include methoxyethyl, ethoxyethyl, methoxypropyl, ethoxypropyl, methylthioethyl, ethylthioethyl and the like.

Examples of lower alkoxycarbonyl-lower alkyl groups include methoxycarbonylmethyl, ethoxycarbonylmethyl, 1-methoxycarbonylethyl, propoxycarbonylmethyl and the like.

Examples of lower alkoxy groups include methoxy, ethoxy, propoxy and the like.

Examples of lower alkoxycarbonyl groups include methoxycarbonyl, ethoxycarbonyl, propoxycarbonyl and the like.

Examples of aralkyl groups include benzyl, 2-phenylethyl, 3-phenylpropyl, 4-phenylbutyl and the like, which may be substituted on the aromatic nucleus by lower alkyl group having 1–3 carbon atoms, trifluoromethyl group or halogen atom.

Examples of haloalkyl groups include trifluoromethyl, difluoromethyl, fluoromethyl, chloromethyl, chloroethyl, chloropropyl, bromoethyl and the like.

Examples of cycloalkyl groups include cyclopropyl, cyclobutyl, cyclopentyl, cyclohexyl and the like.

Halogen atoms include chlorine, bromine, fluorine and iodine atoms.

Examples of aryl groups include phenyl and naphthyl.

Then, interesting compounds included in this invention are as follows:

4-butoxy-N-(2,6-diethylphenyl)-2,6-dimethyl-3-pyridinecarboxamide, 4-ethoxy-2,6-dimethyl-N-phenyl-3-pyridinecarboxamide, 4-allyloxy-2,6-dimethyl-N-phenyl-3-pyridinecarboxamide, 4-benzyloxy-2,6-dimethyl-N-phenyl-3-pyridinecarboxamide, 4-methoxycarbonylmethoxy-2,6-dimethyl-N-phenyl-3-pyridinecarboxamide, N-(2,6-diethylphenyl)-2,6-dimethyl-4-propoxy-3-pyridine-carboxamide, 4-benzyloxy-N-(2,6-diethylphenyl)-2,6-dimethyl-3-pyridinecarboxamide, N-(2,6-diethylphenyl)-2,6-dimethyl-4-phenethyloxy-3-pyridinecarboxamide, 5-bromo-4-butoxy-N-(2,6-diethylphenyl)-2,6-dimethyl-3-pyridinecarboxamide, N-(2-chlorophenyl)-2,6-dimethyl-4-propoxy-3-pyridinecarboxamide, 2,6-dimethyl-N-(2,3-dimethylphenyl)-4-propoxy-3-pyridinecarboxamide, 2,6-dimethyl-N-(2-methylphenyl)-4-propoxy-3-pyridinecarboxamide, 2,6-dimethyl-N-(2,6-dimethylphenyl)-4-propoxy-3-pyridinecarboxamide, 4-ethoxy-2,6-dimethyl-N-(2,3-dimethylphenyl)-3-pyridinecarboxamide, 4-butoxy-2,6-dimethyl-N-(2,3-dimethylphenyl)-3-pyridinecarboxamide, 2,6-dimethyl-N-(2,3-dimethylphenyl)-4-(2-propynyloxy)-3-pyridinecarboxamide, 4-allyloxy-2,6-dimethyl-N-(2,3-dimethylphenyl)-3-pyridinecarboxamide, 4-methoxy-2,6-dimethyl-N-phenyl-3-pyridinecarboxamide, 2,6-dimethyl-N-phenyl-4-propoxy-3-pyridinecarboxamide, 4-butoxy-2,6-dimethyl-N-phenyl-3-pyridinecarboxamide, 4-isobutoxy-2,6-dimethyl-N-phenyl-3-pyridinecarboxamide, 2,6-dimethyl-4-pentyloxy-N-phenyl-3-pyridinecarboxamide, 4-isopentyloxy-2,6-dimethyl-N-phenyl-3-pyridinecarboxamide,
4-hexyloxy-2,6-dimethyl-N-phenyl-3-pyridinecarboxamide,
2,6-dimethyl-N-phenyl-4-(2-propynyloxy)-3-pyridinecarboxamide,
5-bromo-2,6-dimethyl-N-phenyl-4-benzyloxy-3-pyridinecarboxamide,
2,6-dimethyl-N-phenyl-4-(2-phenylethoxy)-3-pyridinecarboxamide,
2,6-dimethyl-N-phenyl-4-(3-phenylpropoxy)-3-pyridinecarboxamide,
2,6-dimethyl-N-phenyl-4-(4-phenylbutoxy)-3-pyridinecarboxamide,
4-(3-chlorobenzyloxy)-2,6-dimethyl-N-phenyl-3-pyridinecarboxamide,
4-(4-chlorobenzyloxy)-2,6-dimethyl-N-phenyl-3-pyridinecarboxamide,
2,6-dimethyl-4-(3-methylbenzyloxy)-N-phenyl-3-pyridinecarboxamide,
2,6-dimethyl-4-(4-methylbenzyloxy)-N-phenyl-3-pyridinecarboxamide,
N-(2-chlorophenyl)-4-butoxy-2,6-dimethyl-3-pyridinecarboxamide,
N-(2-chlorophenyl)-4-hexyloxy-2,6-dimethyl-3-pyridinecarboxamide,
4-benzyloxy-N-(2-chlorophenyl)-2,6-dimethyl-3-pyridinecarboxamide,
4-(4-chlorobenzyloxy)-N-(2-chlorophenyl)-2,6-dimethyl-3-pyridinecarboxamide,
N-(2-chlorophenyl)-2,6-dimethyl-4-(4-methylbenzyloxy)-3-pyridinecarboxamide,
N-(2-chloro-6-methylphenyl)-2,6-dimethyl-4-propoxy-3-pyridinecarboxamide,
N-(2-chloro-6-methylphenyl)-4-butoxy-2,6-dimethyl-3-pyridinecarboxamide,
N-(2-chloro-6-methylphenyl)-4-hexyloxy-2,6-dimethyl-3-pyridinecarboxamide,
4-benzyloxy-N-(2-chloro-6-methylphenyl)-2,6-dimethyl-3-pyridinecarboxamide,
N-(2,6-diethylphenyl)-4-methoxy-2,6-dimethyl-3-pyridinecarboxamide,
4-ethoxy-N-(2,6-diethylphenyl)-2,6-dimethyl-3-pyridinecarboxamide,
N-(2,6-diethylphenyl)-4-isobutoxy-2,6-dimethyl-3-pyridinecarboxamide,
N-(2,6-diethylphenyl)-2,6-dimethyl-4-pentyloxy-3-pyridinecarboxamide,
N-(2,6-diethylphenyl)-4-isopentyloxy-2,6-dimethyl-3-pyridinecarboxamide,
N-(2,6-diethylphenyl)-4-hexyloxy-2,6-dimethyl-3-pyridinecarboxamide,
4-allyloxy-N-(2,6-diethylphenyl)-2,6-dimethyl-3-pyridinecarboxamide,
N-(2,6-diethylphenyl)-2,6-dimethyl-4-(2-propynyloxy)-3-pyridinecarboxamide,
N-(2,6-diethylphenyl)-4-methoxycarbonylmethoxy-2,6-dimethyl-3-pyridinecarboxamide,
N-(2,6-diethylphenyl)-2,6-dimethyl-4-(3-phenylpropoxy)-3-pyridinecarboxamide,
N-(2,6-diethylphenyl)-2,6-dimethyl-4-(4-phenylbutoxy)-3-pyridinecarboxamide,
4-(3-chlorobenzyloxy)-N-(2,6-diethylphenyl)-2,6-dimethyl-3-pyridinecarboxamide,
4-(4-chlorobenzyloxy)-N-(2,6-diethylphenyl)-2,6-dimethyl-3-pyridinecarboxamide,
N-(2,6-diethylphenyl)-2,6-dimethyl-4-(3-methylbenzyloxy)-3-pyridinecarboxamide,
N-(2,6-diethylphenyl)-2,6-dimethyl-4-(4-methylbenzyloxy)-3-pyridinecarboxamide,
N-(2-ethyl-6-methylphenyl)-4-methoxy-2,6-dimethyl-3-pyridinecarboxamide,
4-ethoxy-N-(2-ethyl-6-methylphenyl)-2,6-dimethyl-3-pyridinecarboxamide,
N-(2-ethyl-6-methylphenyl)-2,6-dimethyl-4-propoxy-3-pyridinecarboxamide,
4-butoxy-N-(2-ethyl-6-methylphenyl)-2,6-dimethyl-3-pyridinecarboxamide,
N-(2-ethyl-6-methylphenyl)-4-isobutoxy-2,6-dimethyl-3-pyridinecarboxamide,
N-(2-ethyl-6-methylphenyl)-4-hexyloxy-2,6-dimethyl-3-pyridinecarboxamide,
4-allyloxy-N-(2-ethyl-6-methylphenyl)-2,6-dimethyl-3-pyridinecarboxamide,
N-(2-ethyl-6-methylphenyl)-2,6-dimethyl-4-(2-propynyloxy)-3-pyridinecarboxamide,
4-benzyloxy-N-(2-ethyl-6-methylphenyl)-2,6-dimethyl-3-pyridinecarboxamide,
4-(4-chlorobenzyloxy)-N-(2-ethyl-6-methylphenyl)-2,6-dimethyl-3-pyridinecarboxamide,
N-(2-ethyl-6-methylphenyl)-2,6-dimethyl-4-(4-methylbenzyloxy)-3-pyridinecarboxamide,
4-ethoxy-2,6-dimethyl-N-(2-methylphenyl)-3-pyridinecarboxamide,
4-butoxy-2,6-dimethyl-N-(2-methylphenyl)-3-pyridinecarboxamide,
4-isobutoxy-2,6-dimethyl-N-(2-methylphenyl)-3-pyridinecarboxamide,
4-hexyloxy-2,6-dimethyl-N-(2-methylphenyl)-3-pyridinecarboxamide,
4-allyloxy-2,6-dimethyl-N-(2-methylphenyl)-3-pyridinecarboxamide,
4-benzyloxy-2,6-dimethyl-N-(2-methylphenyl)-3-pyridinecarboxamide,
4-(4-chlorobenzyloxy)-2,6-dimethyl-N-(2-methylphenyl)-3-pyridinecarboxamide,
2,6-dimethyl-4-(4-methylbenzyloxy)-N-(2-methylphenyl)-3-pyridinecarboxamide,
4-isobutoxy-2,6-dimethyl-N-(2,3-dimethylphenyl)-3-pyridinecarboxamide,
4-hexyloxy-2,6-dimethyl-N-(2,3-dimethylphenyl)-3-pyridinecarboxamide,
4-benzyloxy-2,6-dimethyl-N-(2,3-dimethylphenyl)-3-pyridinecarboxamide,
4-(4-chlorobenzyloxy)-2,6-dimethyl-N-(2,3-dimethylphenyl)-3-pyridinecarboxamide,
2,6-dimethyl-4-(4-methylbenzyloxy)-N-(2,3-dimethylphenyl)-3-pyridinecarboxamide,
4-methoxy-2,6-dimethyl-N-(2,6-dimethylphenyl)-3-pyridinecarboxamide,
4-ethoxy-2,6-dimethyl-N-(2,6-dimethylphenyl)-3-pyridinecarboxamide,
4-butoxy-2,6-dimethyl-N-(2,6-dimethylphenyl)-3-pyridinecarboxamide,
4-butoxy-2,6-dimethyl-N-(2,5-dimethylphenyl)-3-pyridinecarboxamide,
4-isobutoxy-2,6-dimethyl-N-(2,6-dimethylphenyl)-3-pyridinecarboxamide,
2,6-dimethyl-N-(2,6-dimethylphenyl)-4-pentyloxy-3-pyridinecarboxamide,
4-isopentyloxy-2,6-dimethyl-N-(2,6-dimethylphenyl)-3-pyridinecarboxamide,
4-hexyloxy-2,6-dimethyl-N-(2,6-dimethylphenyl)-3-pyridinecarboxamide,
4-allyloxy-2,6-dimethyl-N-(2,6-dimethylphenyl)-3-pyridinecarboxamide, 2,6-dimethyl-N-(2,6-dimethylphenyl)-4-(2-propynyloxy)-3-pyridinecarboxamide,
4-benzyloxy-2,6-dimethyl-N-(2,6-dimethylphenyl)-3-pyridinecarboxamide,
4-(4-chlorobenzyloxy)-2,6-dimethyl-N-(2,6-dimethylphenyl)-3-pyridinecarboxamide,
2,6-dimethyl-4-(4-methylbenzyloxy)-N-(2,6-dimethylphenyl)-3-pyridinecarboxamide,
N-(2,6-diisopropylphenyl)-2,6-dimethyl-4-propoxy-3-pyridinecarboxamide,
4-butoxy-N-(2,6-diisopropylphenyl)-2,6-dimethyl-3-pyridinecarboxamide,
N-(2,6-diisopropylphenyl)-4-hexyloxy-2,6-dimethyl-3-pyridinecarboxamide,
4-allyloxy-N-(2,6-diisopropylphenyl)-2,6-dimethyl-3-pyridinecarboxamide,
4-benzyloxy-N-(2,6-diisopropylphenyl)-2,6-dimethyl-3-pyridinecarboxamide,
4-(4-chlorobenzyloxy)-N-(2,6-diisopropylphenyl)-2,6-dimethyl-3-pyridinecarboxamide,
N-(2,6-diisopropylphenyl)-2,6-dimethyl-4-(4-methylbenzyloxy)-3-pyridinecarboxamide,
5-bromo-N-(2,6-diethylphenyl)-2,6-dimethyl-4-propoxy-3-pyridinecarboxamide,
5-bromo-N-(2,6-diethylphenyl)-4-isobutoxy-2,6-dimethyl-3-pyridinecarboxamide,
5-bromo-N-(2,6-diethylphenyl)-2,6-dimethyl-4-pentyloxy-3-pyridinecarboxamide,
5-bromo-N-(2,6-diethylphenyl)-4-isopentyloxy-2,6-dimethyl-3-pyridinecarboxamide,
5-bromo-N-(2,6-diethylphenyl)-4-hexyloxy-2,6-dimethyl-3-pyridinecarboxamide,
4-allyloxy-5-bromo-N-(2,6-diethylphenyl)-2,6-dimethyl-3-pyridinecarboxamide,
5-bromo-N-(2-ethyl-6-methylphenyl)-2,6-dimethyl-4-propoxy-3-pyridinecarboxamide,
5-bromo-4-butoxy-N-(2-ethyl-6-methylphenyl)-2,6-dimethyl-3-pyridinecarboxamide,
5-bromo-N-(2-ethyl-6-methylphenyl)-4-hexyloxy-2,6-dimethyl-3-pyridinecarboxamide,
5-bromo-2,6-dimethyl-N-(2,6-dimethylphenyl)-4-propoxy-3-pyridinecarboxamide,
5-bromo-4-butoxy-2,6-dimethyl-N-(2,6-dimethylphenyl)-3-pyridinecarboxamide,
5-bromo-4-isobutoxy-2,6-dimethyl-N-(2,6-dimethylphenyl)-3-pyridinecarboxamide,
5-bromo-2,6-dimethyl-N-(2,6-dimethylphenyl)-4-pentyloxy-3-pyridinecarboxamide,
5-bromo-4-isopentyloxy-2,6-dimethyl-N-(2,6-dimethylphenyl)-3-pyridinecarboxamide,
5-bromo-4-hexyloxy-2,6-dimethyl-N-(2,6-dimethylphenyl)-3-pyridinecarboxamide,
4-allyloxy-5-bromo-2,6-dimethyl-N-(2,6-dimethylphenyl)-3-pyridinecarboxamide,
5-bromo-2,6-dimethyl-N-(2,6-dimethylphenyl)-4-(2-propynyloxy)-3-pyridinecarboxamide,
5-bromo-N-(2,6-diisopropylphenyl)-2,6-dimethyl-4-propoxy-3-pyridinecarboxamide,
5-bromo-4-butoxy-N-(2,6-diisopropylphenyl)-2,6-dimethyl-3-pyridinecarboxamide,
5-bromo-4-hexyloxy-N-(2,6-diisopropylphenyl)-2,6-dimethyl-3-pyridinecarboxamide,
4-benzyloxy-5-bromo-N-(2,6-diethylphenyl)-2,6-dimethyl-3-pyridinecarboxamide,
4-benzyloxy-5-bromo-N-(2-ethyl-6-methylphenyl)-2,6-dimethyl-3-pyridinecarboxamide,
4-benzyloxy-5-bromo-2,6-dimethyl-N-(2,6-dimethylphenyl)-3-pyridinecarboxamide,
4-benzyloxy-5-bromo-N-(2,6-diisopropylphenyl)-2,6-dimethyl-3-pyridinecarboxmide,
5-chloro-N-(2,6-diethylphenyl)-2,6-dimethyl-4-propoxy-3-pyridinecarboxamide,
4-butoxy-5-chloro-N-(2,6-diethylphenyl)-2,6-dimethyl-3-pyridinecarboxamide,
5-chloro-N-(2,6-diethylphenyl)-4-hexyloxy-2,6-dimethyl-3-pyridinecarboxamide,
4-allyloxy-5-chloro-N-(2,6-diethylphenyl)-2,6-dimethyl-3-pyridinecarboxamide,
4-butoxy-5-chloro-N-(2-ethyl-6-methylphenyl)-2,6-dimethyl-3-pyridinecarboxamide,
5-chloro-N-(2-ethyl-6-methylphenyl)-4-hexyloxy-2,6-dimethyl-3-pyridinecarboxamide,
4-butoxy-5-chloro-2,6-dimethyl-N-(2,6-dimethylphenyl)-3-pyridine carboxamide,
5-chloro-4-hexyloxy-2,6-dimethyl-N-(2,6-dimethylphenyl)-3-pyridinecarboxamide,
4-butoxy-5-chloro-N-(2,6-diisopropylphenyl-2,6-dimethyl-3-pyridinecarboxamide,
5-chloro-4-hexyloxy-N-(2,6-diisopropylphenyl)-2,6-dimethyl-3-pyridinecarboxamide,
2,6-dimethyl-N-(2,3-dimethylphenyl)-4-pentyloxy-3-pyridinecarboxamide,
4-isopentyloxy-2,6-dimethyl-N-(2,3-dimethylphenyl)-3-pyridinecarboxamide,
2,6-dimethyl-N-(2,3-dimethylphenyl)-4-octyloxy-3-pyridinecarboxamide,
2,6-dimethyl-N-(2,3-dimethylphenyl)-4-(2-phenylethyloxy)-3-pyridinecarboxamide,
4-cyclohexylmethyloxy-2,6-dimethyl-N-(2,3-dimethylphenyl)-3-pyridinecarboxamide,
N-(2,6-diethylphenyl)-4-isopropoxy-2,6-dimethyl-3-pyridinecarboxamide,
4-ethoxycarbonylmethyloxy-N-(2,6-diethylphenyl)-2,6-dimethyl-3-pyridinecarboxamide,
4-(1-ethoxycarbonylethyloxy)-N-(2,6-diethyphenyl)-2,6-dimethyl-3-pyridinecarboxamide,
2,6-dimethyl-N-phenyl-4-propoxy-3-pyridinecarboxamide 1-oxide,
4-butoxy-2,6-dimethyl-N-phenyl-3-pyridinecarboxamide 1-oxide,
2,6-dimethyl-N-(2-methylphenyl)-4-propoxy-3-pyridinecarboxamide 1-oxide,
2,6-dimethyl-N-(2,3-dimethylphenyl)-4-propoxy-3-pyridinecarboxamide 1-oxide,
4-butoxy-2,6-dimethyl-N-(2,3-dimethylphenyl)-3-pyridinecarboxamide 1-oxide,
4-isobutoxy-2,6-dimethyl-N-(2,3-dimethylphenyl)-3-pyridinecarboxamide 1-oxide,
2,6-dimethyl-N-(2,3-dimethylphenyl)-4-pentyloxy-3-pyridnecarboxamide 1-oxide,
4-isopentyloxy-2,6-dimethyl-N-(2,3-dimethylphenyl)-3-pyridinecarboxamide 1-oxide,
4-hexyloxy-2,6-dimethyl-N-(2,3-dimethylphenyl)-3-pyridinecarboxamide 1-oxide,
2,6-dimethyl-N-(2,3-dimethylphenyl)-4-octyloxy-3-pyridinecarboxamide 1-oxide,
4-(2-ethoxyethoxy)-2,6-dimethyl-N-(2,3-dimethylphenyl)-3-pyridinecarboxamide 1-oxide,
4-allyloxy-2,6-dimethyl-N-(2,3-dimethylphenyl)-3-pyridinecarboxamide 1-oxide,
2,6-dimethyl-N-(2,6-dimethylphenyl)-4-propoxy-3-pyridinecarboxamide 1-oxide,
4-ethoxy-N-(2,6-diethylphenyl)-2,6-dimethyl-3-pyridinecarboxamide 1-oxide,
N-(2,6-diethylphenyl)-2,6-dimethyl-4-propoxy-3-pyridinecarboxamide 1-oxide, N-(2,6-diethylphenyl)-4-isopropoxy-2,6-dimethyl-3-pyridinecarboxamide 1-oxide,
4-butoxy-N-(2,6-diethylphenyl)-2,6-dimethyl-3-pyridinecarboxamide 1-oxide,
N-(2,6-diethylphenyl)-4-isobutoxy-2,6-dimethyl-3-pyridinecarboxamide 1-oxide,
N-(2,6-diethylphenyl)-2,6-dimethyl-4-pentyloxy-3-pyridinecarboxamide 1-oxide,
4-benzyloxy-N-(2,6-diethylphenyl)-2,6-dimethyl-3-pyridinecarboxamide 1-oxide,
4-ethoxycarbonylmethoxy-N-(2,6-diethylphenyl)-2,6-dimethyl-3-pyridinecarboxamide 1-oxide,
4-(1-ethoxycarbonylethoxy)-N-(2,6-diethylphenyl)-2,6-dimethyl-3-pyridinecarboxamide 1-oxide,
N-(2-methoxyphenyl)-2,6-dimethyl-4-propoxy-3-pyridinecarboxamide 1-oxide,
2,6-dimethyl-N-(3-nitrophenyl)-4-propoxy-3-pyridinecarboxamide 1-oxide,
6-methyl-N, 2-diphenyl-4-propoxy-3-pyridinecarboxamide 1-oxide,
5-bromo-N-(2,6-diethylphenyl)-2,6-dimethyl-4-propoxy-3-pyridinecarboxamide 1-oxide,
4-ethoxy-2,6-dimethyl-N-phenyl-3-pyridinecarboxamide 1-oxide,
4-isopropoxy-2,6-dimethyl-N-phenyl-3-pyridinecarboxamide 1-oxide,
4-isobutoxy-2,6-dimethyl-N-phenyl-3-pyridinecarboxamide 1-oxide,
2,6-dimethyl-4-pentyloxy-N-phenyl-3-pyridinecarboxamide 1-oxide,
4-isopentyloxy-2,6-dimethyl-N-phenyl-3-pyridinecarboxamide 1-oxide, 4-allyloxy-2,6-dimethyl-N-phenyl-3-pyridinecarboxamide 1-oxide,
2,6-dimethyl-N-phenyl-4-(2-propynyloxy)-3-pyridinecarboxamide 1-oxide,
4-methoxy-2,6-dimethyl-N-(2,3-dimethylphenyl)-3-pyridinecarboxamide 1-oxide,
4-ethoxy-2,6-dimethyl-N-(2,3-dimethylphenyl)-3-pyridinecarboxamide 1-oxide,
4-isopropoxy-2,6-dimethyl-N-(2,3-dimethylphenyl)-3-pyridinecarboxamide 1-oxide,
2,6-dimethyl-N-(2,3-dimethylphenyl)-4-(2-propynyloxy)-3-pyridinecarboxamide 1-oxide,
4-benzyloxy-2,6-dimethyl-N-(2,3-dimethylphenyl)-3-pyridinecarboxamide 1-oxide,
2,6-dimethyl-N-(2,3-dimethylphenyl)-4-(2-phenylethoxy)-3-pyridinecarboxamide 1-oxide,
4-cyclohexylmethoxy-2,6-dimethyl-N-(2,3-dimethylphenyl)-3-pyridinecarboxamide 1-oxide,
4-(2-chloroethoxy)-2,6-dimethyl-N-(2,3-dimethylphenyl)-3-pyridinecarboxamide 1-oxide,
N-(2,6-diethylphenyl)-4-methoxy-2,6-dimethyl-3-pyridinecarboxamide 1-oxide,
N-(2,6-diethylphenyl)-4-isopentyloxy-2,6-dimethyl-3-pyridinecarboxamide 1-oxide,
4-allyloxy-N-(2,6-diethylphenyl)-2,6-dimethyl-3-pyridinecarboxamide 1-oxide,
N-(2,6-diethylphenyl)-2,6-dimethyl-4-(2-propynyloxy)-3-pyridinecarboxamide 1-oxide,
N-(2,6-diethylphenyl)-2,6-dimethyl-4-(2-phenylethoxy)-3-pyridinecarboxamide 1-oxide,
4-cyclohexylmethoxy-N-(2,6-diethylphenyl)-2,6-dimethyl-3-pyridinecarboxamide 1-oxide,
4-(2-chloroethoxy)-N-(2,6-diethylphenyl)-2,6-dimethyl-3-pyridinecarboxamide 1-oxide,
N-(2-chlorophenyl)-2,6-dimethyl-4-propoxy-3-pyridinecarboxamide 1-oxide,
4-butoxy-N-(3-trifluoromethylphenyl)-2,6-dimethyl-3-pyridinecarboxamide 1-oxide,
N-(2-chloro-6-methylphenyl)-4-isobutyloxy-2,6-dimethyl-3-pyridinecarboxamide 1-oxide,
N-(2-ethyl-6-methylphenyl)-4-isopentyloxy-2,6-dimethyl-3-pyridinecarboxamide 1-oxide,
4-allyloxy-N-(2,6-dichlorophenyl)-2,6-dimethyl-3-pyridinecarboxamide 1-oxide,
N-(4-bromo-2,6-diethylphenyl)-2,6-dimethyl-4-propoxy-3-pyridinecarboxamide 1-oxide,
4-butoxy-N-(4-bromo-2,6-diethylphenyl)-2,6-dimethyl-3-pyridinecarboxamide 1-oxide,
N-(4-bromo-2,6-diethylphenyl)-4-isobutoxy-2,6-dimethyl-3-pyridinecarboxamide 1-oxide,
N-(4-bromo-2,6-diethylphenyl)-2,6-dimethyl-4-pentyloxy-3-pyridinecarboxamide 1-oxide,
N-(4-bromo-2,6-diethylphenyl)-4-isopentyloxy-2,6-dimethyl-3-pyridinecarboxamide 1-oxide,
4-allyloxy-N-(4-bromo-2,6-diethylphenyl)-2,6-dimethyl-3-pyridinecarboxamide 1-oxide,
N-(4-chloro-2,6-diethylphenyl)-2,6-dimethyl-4-propoxy-3-pyridinecarboxamide 1-oxide,
4-butoxy-N-(4-chloro-2,6-diethylphenyl)-2,6-dimethyl-3-pyridinecarboxamide 1-oxide,
N-(4-chloro-2,6-diethylphenyl)-4-isobutoxy-2,6-dimethyl-3-pyridinecarboxamide 1-oxide,
N-(4-chloro-2,6-diethylphenyl)-2,6-dimethyl-4-pentyloxy-3-pyridinecarboxamide 1-oxide,
N-(4-chloro-2,6-diethylphenyl)-4-isopentyloxy-2,6-dimethyl-3-pyridinecarboxamide 1-oxide,
4-allyloxy-N-(4-chloro-2,6-diethylphenyl)-2,6-dimethyl-3-pyridinecarboxamide 1-oxide,
6-methyl-N-(2,3-dimethylphenyl)-2-phenyl-4-propoxy-3-pyridinecarboxamide 1-oxide,
4-butoxy-6-methyl-N-(2,3-dimethylphenyl)-2-phenyl-3-pyridinecarboxamide 1-oxide,
4-isobutoxy-6-methyl-N-(2,3-dimethylphenyl)-2-phenyl-3-pyridinecarboxamide 1-oxide,
4-isopentyloxy-6-methyl-N-(2,3-dimethylphenyl)-2-phenyl-3-pyridinecarboxamide 1-oxide,
4-allyloxy-6-methyl-N-(2,3-dimethylphenyl)-2-phenyl-3-pyridinecarboxamide 1-oxide,
N-(2,6-diethylphenyl)-6-methyl-2-phenyl-4-propoxy-3-pyridinecarboxamide 1-oxide,
4-butoxy-N-(2,6-diethylphenyl)-6-methyl-2-phenyl-3-pyridinecarboxamide 1-oxide,
N-(2,6-diethylphenyl)-4-isobutoxy-6-methyl-2-phenyl-3-pyridinecarboxamide 1-oxide,
N-(2,6-diethylphenyl)-4-isopentyloxy-6-methyl-2-phenyl-3-pyridinecarboxamide 1-oxide,
4-allyloxy-N-(2,6-diethylphenyl)-6-methyl-2-phenyl-3-pyridinecarboxamide 1-oxide,
N-(4-bromo-2,6-diethylphenyl)-6-methyl-6-methyl-2-phenyl-4-propoxy-3-pyridinecarboxamide 1-oxide,
N-(4-bromo-2,6-diethylphenyl)-4-butoxy-6-methyl-2-phenyl-3-pyridinecarboxamide 1-oxide,
5-bromo-N-(2,6-diethylphenyl)-4-isobutoxy-2,6-dimethyl-3-pyridinecarboxamide 1-oxide,
5-bromo-N-(2,6-diethylphenyl)-4-isopentyloxy-2,6-dimethyl-3-pyridinecarboxamide 1-oxide,
5-bromo-N-(4-bromo-2,6-diethylphenyl)-2,6-dimethyl-4-propoxy-3-pyridinecarboxamide 1-oxide,
4-butoxy-5-chloro-N-(2,6-diethylphenyl)-2,6-dimethyl-3-pyridinecarboxamide 1-oxide,
4-allyloxy-5-chloro-N-(2,6-diethylphenyl)-2,6-dimethyl-3-pyridinecarboxamide 1-oxide,
5-chloro-N-(4-chloro-2,6-diethylphenyl)-2,6-dimethyl-4-propoxy-3-pyridinecarboxamide 1-oxide, 2-ethyl-6-methyl-N-(2,3-dimethylphenyl)-4-propoxy-3-pyridinecarboxamide 1-oxide, 4-butoxy-2-ethyl-6-methyl-N-(2,3-dimethylphenyl)-3-pyridinecarboxamide 1-oxide, 2-ethyl-N-(2,6-diethylphenyl)-6-methyl-4-propoxy-3-pyridinecarboxamide 1-oxide, 2-ethyl-N-(2,6-diethylphenyl)-4-isopropoxy-6-methyl-3-pyridinecarboxamide 1-oxide, 6-methyl-N-(2,3-dimethylphenyl)-4-propoxy-2-propyl-3-pyridinecarboxamide 1-oxide, 4-isopentyloxy-6-methyl-N-(2,3-dimethylphenyl)-2-propyl-3-pyridinecarboxamide 1-oxide, N-(2,6-diethylphenyl)-6-methyl-4-propoxy-2-propyl-3-pyridinecarboxamide 1-oxide, 4-allyloxy-N-(2,6-diethylphenyl)-6-methyl-2-propyl-3-pyridinecarboxamide 1-oxide, 6-methyl-N-(2,3-dimethylphenyl)-2-phenylmethyl-4-propoxy-3-pyridinecarboxamide 1-oxide, 4-butoxy-6-methyl-N-(2,3-dimethylphenyl)-2-phenylmethyl-3-pyridinecarboxamide 1-oxide, N-(2,6-diethylphenyl)-6-methyl-2-phenylmethyl-4-propoxy-3-pyridinecarboxamide 1-oxide, N-(2,6-diethylphenyl)-4-isobutoxy-6-methyl-2-phenylmethyl-3-pyridinecarboxamide 1-oxide, 2-trifluoromethyl-6-methyl-N-(2,3-dimethylphenyl)-4-propoxy-3-pyridinecarboxamide 1-oxide, 2-trifluoromethyl-4-isopentyloxy-6-methyl-N-(2,3-dimethylphenyl)-3-pyridinecarboxamide 1-oxide, N-(2,6-diethylphenyl)-2-trifluoromehtyl-6-methyl-4-propoxy-3-pyridinecarboxamide 1-oxide, 4-allyloxy-N-(2,6-diethylphenyl)-2-trifluoromethyl-6-methyl-3-pyridinecarboxamide 1-oxide, 4-butoxy-6-methyl-N-(2,3-dimethylphenyl)-2-propyl-3-pyridinecarboxamide 1-oxide, 2-ethyl-4-isobutoxy-6-methyl-N-(2,3-dimethylphenyl)-3-pyridinecarboxamide 1-oxide, 4-isobutoxy-6-methyl-N-(2,3-dimethylphenyl)-2-propyl-3-pyridinecarboxamide 1-oxide, 2-ethyl-4-isopentyloxy-6-N-(2,3-dimethylphenyl)-3-pyridinecarboxamide 1-oxide, 4-allyloxy-2-ethyl-6-methyl-N-(2,3-dimethylphenyl)-3-pyridinecarboxamide 1-oxide, 4-allyloxy-6-methyl-N-(2,3-dimethylphenyl)-2-propyl-3-pyridinecarboxamide 1-oxide, 4-butoxy-2-ethyl-N-(2,6-diethylphenyl)-6-methyl-3-pyridinecarboxamide 1-oxide, 4-butoxy-N-(2,6-diethylphenyl)-6-methyl-2-propyl-3-pyridinecarboxamide 1-oxide, N-(2,6-diethylphenyl)-4-isobutoxy-6-methyl-2-propyl-3-pyridinecarboxamide 1-oxide, 2-ethyl-N-(2,6-diethylphenyl)-4-isopentyloxy-6-methyl-3-pyridinecarboxamide 1-oxide, N-(2,6-diethylphenyl)-4-isopentyloxy-6-methyl-2-propyl-3-pyridinecarboxamide 1-oxide, 4-allyloxy-2-ethyl-N-(2,6-diethylphenyl)-6-methyl-3-pyridinecarboxamide 1-oxide, 4-butoxy-2-trifluoromethyl-6-methyl-N-(2,3-dimethylphenyl)-3-pyridinecarboxamide 1-oxide, 4-isobutoxy-6-methyl-N-(2,3-dimethylphenyl)-2-phenylmethyl-3-pyridinecarboxamide 1-oxide, 2-trifluoromethyl-4-isobutoxy-6-methyl-N-(2,3-dimethylphenyl)-3-pyridinecarboxamide 1-oxide, 4-isopentyloxy-6-methyl-N-(2,3-dimethylphenyl)-2-phenylmethyl-3-pyridinecarboxamide 1-oxide, 4-allyloxy-6-methyl-N-(2,3-dimethylphenyl)-2-phenylmethyl-3-pyridinecarboxamide 1-oxide, 4-allyloxy-2-trifluoromethyl-6-methyl-N-(2,3-dimethylphenyl)-3-pyridinecarboxamide 1-oxide, 4-butoxy-N-(2,6-diethylphenyl)-6-methyl-2-phenylmethyl-3-pyridinecarboxamide 1-oxide, 4-butoxy-N-(2,6-diethylphenyl)-2-trifluoromethyl-6-methyl-3-pyridinecarboxamide 1-oxide, N-(2,6-diethylphenyl)-2-trifluoromethyl-4-isobutoxy-6-methyl-3-pyridinecarboxamide 1-oxide, N-(2,6-diethylphenyl)-4-isopentyloxy-6-methyl-2-phenylmethyl-3-pyridinecarboxamide 1-oxide, N-(2,6-diethylphenyl)-2-trifluoromethyl-4-isopentyloxy-6-methyl-3-pyridinecarboxamide 1-oxide, 4-allyloxy-N-(2,6-diethylphenyl)-6-methyl-2-phenylmethyl-3-pyridinecarboxamide 1-oxide, 4-(2-ethylthioethoxy)-N-(2,6-diethylphenyl)-2,6-dimethyl-3-pyridinecarboxamide 1-oxide, 2-cyclohexyl-6-methyl-N-(2,3-dimethylphenyl)-4-propoxy-3-pyridinecarboxamide 1-oxide, 6-methyl-N-(2,3-dimethylphenyl)-2-(2-methylphenyl)-4-propoxy-3-pyridinecarboxamide 1-oxide, 6-methyl-N-(2,3-dimethylphenyl)-2-(3-methylphenyl)-4-propoxy-3-pyridinecarboxamide 1-oxide, 6-methyl-N-(2,3-dimethylphenyl)-2-(4-methylphenyl)-4-propoxy-3-pyridinecarboxamide 1-oxide, 2-(2-chlorophenyl)-N-(2,6-diethylphenyl)-6-methyl-4-propoxy-3-pyridinecarboxamide 1-oxide, 2-(3-chlorophenyl)-N-(2,6-diethylphenyl)-6-methyl-4-propoxy-3-pyridinecarboxamide 1-oxide, N-(2,6-diethylphenyl)-2-(3-trifluoromethylphenyl)-6-methyl-4-propoxy-3-pyridinecarboxamide 1-oxide, N-(2,6-diethylphenyl)-2-(4-methoxyphenyl)-6-methyl-4-propoxy-3-pyridinecarboxamide 1-oxide, 2-(3-cyanophenyl)-N-(2,6-diethylphenyl)-6-methyl-4-propoxy-3-pyridinecarboxamide 1-oxide, N-(2,6-diethylphenyl)-6-methyl-2-(3-nitrophenyl)-4-propoxy-3-pyridinecarboxamide 1-oxide, N-(2-methoxycarbonylphenyl)-2,6-dimethyl-4-propoxy-3-pyridinecarboxamide 1-oxide, N-(4-cyanophenyl)-2,6-dimethyl-4-propoxy-3-pyridinecarboxamide 1-oxide, 2,6-dimethyl-N-(2,4,6-trimethylphenyl)-4-propoxy-3-pyridinecarboxamide 1-oxide, N-(2,6-diethyl-4-methylphenyl)-2,6-dimethyl-4-propoxy-3-pyridinecarboxamide 1-oxide, N-(2,4,6-triethylphenyl)-2,6-dimethyl-4-propoxy-3-pyridinecarboxamide 1-oxide, N-(2-methoxyphenyl)-2,6-dimethyl-4-propoxy-3-pyridinecarboxamide, 2,6-dimethyl-N-(3-nitrophenyl)-4-propoxy-3-pyridinecarboxamide, 4-(2-ethoxyethoxy)-2,6-dimethyl-N-(2,3-dimethylphenyl)-3-pyridinecarboxamide, 4-(2-chloroethoxy)-2,6-dimethyl-N-(2,3-dimethylphenyl)-3-pyridinecarboxamide, N-(4-bromo-2,6-diethylphenyl)-2,6-dimethyl-4-propoxy-3-pyridinecarboxamide, 6-methyl-N,2-diphenyl-4-propoxy-3-pyridinecarboxamide, 6-methyl-N-(2,3-dimethylphenyl)-2-phenyl-4-propoxy-3-pyridinecarboxamide, N-(2,6-diethylphenyl)-6-methyl-2-phenyl-4-propoxy-3-pyridinecarboxamide, N-(4-bromo-2,6-diethylphenyl)-4-butoxy-2,6-dimethyl-3-pyridinecarboxamide, 2-ethyl-N-(2,6-diethylphenyl)-6-methyl-4-propoxy-3-pyridinecarboxamide, 5-bromo-N-(4-bromo-2,6-diethylphenyl)-2,6-dimethyl-4-propoxy-3-pyridinecarboxamide, N-(2,6-diethylphenyl)-2,5,6-trimethyl-4-propoxy-3-pyridinecarboxamide, 4-butoxy-2,5,6-trimethyl-N-phenyl-3-pyridinecarboxamide, 2,6-diethyl-N-(2,6-diethylphenyl)-4-propoxy-3-pyridinecarboxamide, N-(2,6-diethylphenyl)-2-methyl-6-phenyl-4-propoxy-3-pyridinecarboxamide, N-(2,6-diethylphenyl)-5,6,7,8-tetrahydro-2-methyl-4-propoxy-3-quinolinecarboxamide, 6-butyl-N-(2,6-diethylphenyl)-2-methyl-4-propoxy-3-pyridinecarboxamide, N-(2,6-diethylphenyl)-2,6-dimethyl-4-(2-phenylethyloxy)-3-pyridinecarboxamide 1-oxide, 5-bromo-N-(4-bromo-2,6-diethylphenyl)-2,6-dimethyl-4-propoxy-3-pyridinecarboxamide 1-oxide, 2-ethyl-N-(2,6-diethylphenyl)-6-methyl-4-propoxy-3-pyridinecarboxamide 1-oxide, N-(2,6-diethylphenyl)-2,5,6-trimethyl-4-propoxy-3-pyridinecarboxamide 1-oxide, 2,6-diethyl-N-(2,6-diethylphenyl)-4-propoxy-3-pyridinecarboxamide 1-oxide, 4-butoxy-2,5,6-trimethyl-N-phenyl-3-pyridinecarboxamide 1-oxide, 6-butyl-N-(2,6-diethylphenyl)-2-methyl-4-propoxy-3-pyridinecarboxamide 1-oxide, N-(2,6-diethylphenyl)-5,6,7,8-tetrahydro-2-methyl-4-propoxy-3-quinolinecarboxamide 1-oxide, N-(2,6-diethylphenyl)-4-isobutoxy-5,6-dimethyl-2-propyl-3-pyridinecarboxamide 1-oxide, 6-ethyl-N-(2,6-diethylphenyl)-2-methyl-4-propoxy-3-pyridinecarboxamide 1-oxide, 6-ethyl-2-methyl-N-(2,3-dimethylphenyl)-4-propoxy-3-pyridinecarboxamide 1-oxide, 2,6-diethyl-N-(2,3-dimethylphenyl)-4-propoxy-3-pyridinecarboxamide 1-oxide, N-(4-bromo-2,6-diethylphenyl)-2,6-diethyl-4-propoxy-3-pyridinecarboxamide 1-oxide, 2,6-diethyl-N-(2,6-diethylphenyl)-4-isobutoxy-3-pyridinecarboxamide 1-oxide, 4-allyloxy-2,6-diethyl-N-(2,6-diethylphenyl)-3-pyridinecarboxamide 1-oxide, The compounds of the general formula (I) on the 1-oxide thereof according to the present invention may be in the form of addition salt with an acid, such as hydrochloric acid, sulfuric acid, phosphoric acid, methanesulphonic acid, p-toluenesulfonic acid or trifluoroacetic acid. Such addition salts are also included in the present invention.

The compounds of the general formula (I) may be prepared by conducting the following processes successively. (1) A compound of the general formula (IV) is prepared by the reaction of a compound of the general formula (VII) or (VII') with a compound of the general formula (VIII) (Reaction A), or by the reaction of a compound of the general formula (VII) or (VII') with a compound of the general formula (IX) or diketene (Reaction B). (2) And the compound of the general formula (IV) is converted to a compound of the general formula (II) by the reaction of the compound of general formula (IV) with ammonia (Reaction C) or a compound of the general formula (VI) with halogenating agent (Reaction D). (3) And the compound of the general formula (I) is obtained by the reaction of the compound of the general formula (II) with a compound of the general formula (III) (Reaction E).

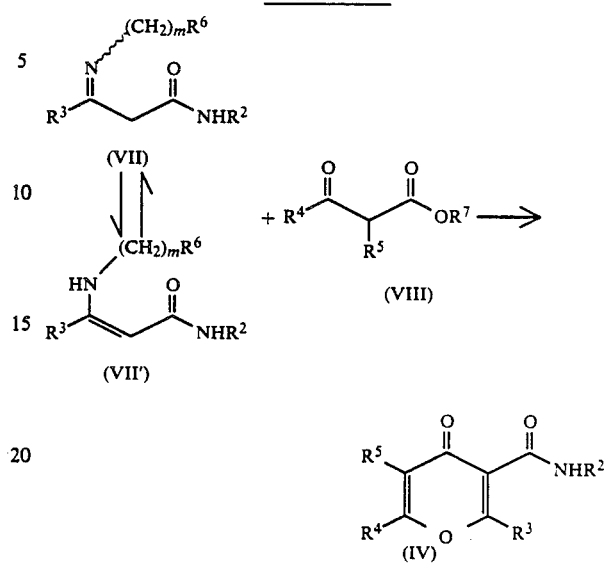

In the above formulae, $R^6$ is dialkylamino group such as dimethylamino, or 1-pyrrolidinyl and the like; m is an integer of from 0 to 6, $R^7$ is alkyl group such as methyl, ethyl and the like; $R^2$, $R^3$, $R^4$ and $R^5$ are as defined in the general formula (I).

The reaction A may be conducted in an inert solvent such as xylene, in the presence of a molecular sieve at 100°–200° C.

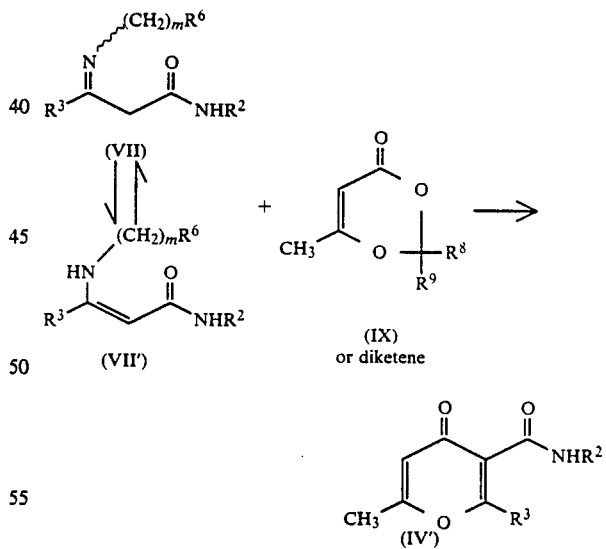

In the above formulae, $R^8$ and $R^9$ are hydrogen, alkyl or phenyl group; when $R^8$ and $R^9$ are alkyl groups, they may form cycloalkyl linkage; $R^2$, $R^3$, $R^6$ and m are as defined before.

The reaction B is specific to a compound of the general formula (IV'), which is the specific one of the general formula (IV) wherein $R^4$ is methyl and $R^5$ is hydrogen.

A preferred compound of the general formula (IX) is 2,2,6-trimethyl-4H-1,3-dioxin-4-one.

The reaction B may be conducted in the presence of an inert solvent such as benzene, toluene or xylene.

The reaction temperature is preferably in the range from 100° C. to 150° C. when the compound of the general formula (IX) is used, and is preferably in the range from −20° C. to 130° C. when diketene is used.

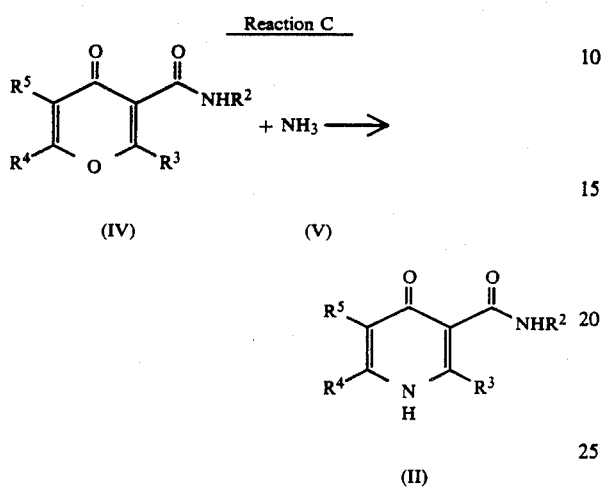

In the formulae, $R^2$–$R^5$ are as defined before.

The reaction C may be conducted in the presence of a solvent such as ethanol or water, at a low temperature such as in the range from room temperature to about 60° C.

The amount of ammonia is equivalent to or more moles than one mole of the compound of the formula (IV) although it may be large excess.

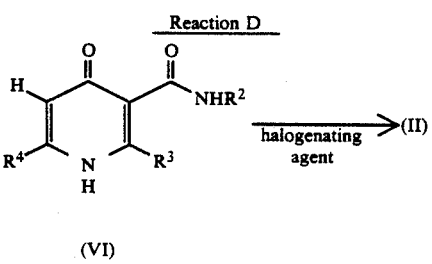

In the formula, $R^2$, $R^3$ and $R^4$ are as defined in the formula (I). The compound of the general formula (II) wherein $R^5$ is halogen atom is obtained by the above reaction D.

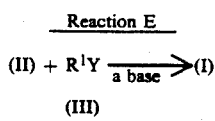

In the above formula, Y is chlorine, bromine or iodine atom.

This reaction may be conducted by reacting 1,4-dihydro-4-oxo-3-pyridinecarboxamide compounds with a halogenated compound in the presence of a base such as potassium carbonate, sodium hydroxide or the like and also in the presence of an appropriate solvent such as N,N-dimethylformamide, dimethylsulfoxide or the like, preferably under heating.

The 1-oxide compound of this invention which is indicated by the general formula (I'), may be obtained by the reaction as follows:

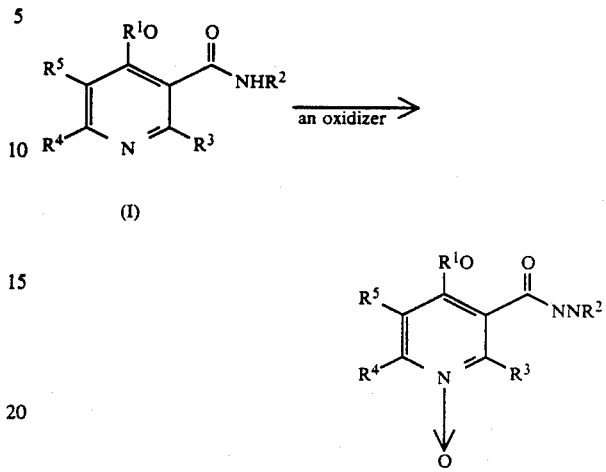

This method is conducted by treating 4-(substituted-oxy)-3-pyridinecarboxamide compound with an oxidizer i.e., hydroperoxide such as hydrogen peroxide, tertiary butyl hydroperoxide or the like, or an organic peracid such as peracetic acid, perbenzoic acid, m-chloroperbenzoic acid or the like in the presence of an appropriate solvent.

This invention is further illustrated by examples hereinafter. The physical properties of the compounds in the examples are indicated in Table-1. The plant growth inhibitory activities of the compounds in the examples are indicated in Table-2.

EXAMPLE 1

4-Butoxy-N-(2,6-diethylphenyl)-2,6-dimethyl-3-pyridinecarboxamide

A mixture of 895 mg (3.0 m mol) of N-(2,6-diethylphenyl)-1,4-dihydro-2,6-dimethyl-4-oxo-3-pyridinecarboxamide, 617 mg (4.5 m mol) of n-butyl bromide, 414 mg (3.0 m mol) of potassium carbonate and 15 ml of N,N-dimethylformamide was stirred for 2 hours at 90° C.

About 50 ml of water was added to the reaction mixture and the mixture was cooled to room temperature to precipitate a solid. The obtained solid was crystallized from a mixture of ethyl acetate and hexane to obtain 870 mg of the title compound (Yield: 82%).

m.p.: 143°–145° C.

EXAMPLES 2–11

The following compounds were obtained from the corresponding 1,4-dihydro-2,6-dimethyl-4-oxo-3-pyridinecarboxamides and the corresponding halogenated compounds in a similar way to the method of Example 1. When boiling point of the halogenated compound employed was lower than 90° C., the reaction however was carried out at refluxing temperature. The halogenated compounds employed as the raw material were mentioned in Table-1.

4-ethoxy-2,6-dimethyl-N-phenyl-3-pyridinecarboxamide (Example 2), 4-allyloxy-2,6-dimethyl-N-phenyl-3-pyridinecarboxamide (Example 3), 4-benzyloxy-2,6-dimethyl-N-phenyl-3-pyridinecarboxamide (Example 4), 4-methoxycarbonylmethoxy-2,6-dimethyl-N-phenyl-3-pyridinecarboxamide (Example 5), N-(2,6-diethylphenyl)-2,6-dimethyl-4-propoxy-3-pyridinecarboxamide (Example 6), 4-benzyloxy-N-(2,6-diethylphenyl)-2,6-diimethyl-3-pyridinecarboxamide (Example 7), N-(2,6-diethylphenyl)-2,6-dimethyl-4-(2-phenylethyloxy)-3-pyridinecarboxamide (Example 8), 5-bromo-4-butoxy-N-(2,6-diethylphenyl)-2,6-dimethyl-3-pyridinecarboxamide (Example 9), N-(2-chlorophenyl)-2,6-dimethyl-4-propoxy-3-pyridinecarboxamide (Example 10), 2,6-dimethyl-N-(2,3-dimethylphenyl)-4-propoxy-3-pyridinecarboxamide (Example 11),

EXAMPLE 12

2,6-Dimethyl-N-phenyl-4-propoxy-3-pyridinecarboxamide

A mixture of 2.42 g (10 m mol) of 1,4-dihydro-2,6-dimethyl-4-oxo-N-phenyl-3-pyridinecarboxamide, 1.84 g (15 m mol) of n-propyl bromide, 1.52 g (11 m mol) of potassium carbonate and 40 ml of N,N-dimethyl formamide was stirred for 7 hours in a bath at 90° C.

About 100 ml of water was added to the reaction mixture. Precipitated crystals were filtered off and dried to obtain 2.14 g of the title compound (Yield: 75.3%)

m.p.: 129°–131° C.

EXAMPLES 13–50

The following compounds were obtained by a similar method to Example 12, from the corresponding 1,4-dihydro-4-oxo-3-pyridinecarboxamides and the corresponding halogenated compounds. The halogenated compounds used as the raw material were mentioned in Table-1.

4-butoxy-2,6-dimethyl-N-phenyl-3-pyridinecarboxamide (Example 13), 2,6-dimethyl-N-(2-methylphenyl)-4-propoxy-3-pyridinecarboxamide (Example 14), 4-ethoxy-2,6-dimethyl-N-(2,3-dimethylphenyl)-3-pyridinecarboxamide (Example 15), 4-butoxy-2,6-dimethyl-N-(2,3-dimethylphenyl)-3-pyridinecarboxamide (Example 16), 4-isobutoxy-2,6-dimethyl-N-(2,3-dimethylphenyl)-3-pyridinecarboxamide (Example 17), 2,6-dimethyl-N-(2,3-dimethylphenyl)-4-pentyloxy-3-pyridinecarboxamide (Example 18), 4-isopentyloxy-2,6-dimethyl-N-(2,3-dimethylphenyl)-3-pyridinecarboxamide (Example 19), 4-hexyloxy-2,6-dimethyl-N-(2,3-dimethylphenyl)-3-pyridinecarboxamide (Example 20), 2,6-dimethyl-N-(2,3-dimethylphenyl)-4-octyloxy-3-pyridinecarboxamide (Example 21), 4-allyloxy-2,6-dimethyl-N-(2,3-dimethylphenyl)-3-pyridinecarboxamide (Example 22), 2,6-dimethyl-N-(2,3-dimethylphenyl)-4-(2-propynyloxy)-3-pyridinecarboxamide (Example 23), 2,6-dimethyl-N-(2,3-dimethylphenyl)-4-(2-phenylethyloxy)-3-pyridinecarboxamide (Example 24), 4-cyclohexylmethyloxy-2,6-dimethyl-N-(2,3-dimethylphenyl)-3-pyridinecarboxamide (Example 25), 2,6-dimethyl-N-(2,6-dimethylphenyl)-4-propoxy-3-pyridinecarboxamide (Example 26), 4-ethoxy-N-(2,6-diethylphenyl)-2,6-dimethyl-3-pyridinecarboxamide (Example 27), N-(2,6-diethylphenyl)-4-isopropoxy-2,6-dimethyl-3-pyridinecarboxamide (Example 28), N-(2,6-diethylphenyl)-4-isobutoxy-2,6-dimethyl-3-pyridinecarboxamide (Example 29), N-(2,6-diethylphenyl)-2,6-dimethyl-4-pentyloxy-3-pyridinecarboxamide (Example 30), 4-ethoxycarbonylmethyloxy-N-(2,6-diethylphenyl)-2,6-dimethyl-3-pyridinecarboxamide (Example 31), 4-(1-ethoxycarbonylethyloxy)-N-(2,6-diethylphenyl)-2,6-dimethyl-3-pyridinecarboxamide (Example 32), 5-bromo-N-(2,6-diethylphenyl)-2,6-dimethyl-4-propoxy-3-pyridinecarboxamide (Example 33), N-(2-methoxyphenyl)-2,6-dimethyl-4-propoxy-3-pyridinecarboxamide (Example 34), 2,6-dimethyl-N-(3-nitrophenyl)-4-propoxy-3-pyridinecarboxamide (Example 35), 4-(2-ethoxyethoxy)-2,6-dimethyl-N-(2,3-dimethylphenyl)-3-pyridinecarboxamide (Example 36), 4-(2-chloroethoxy)-2,6-dimethyl-N-(2,3-dimethylphenyl)-3-pyridinecarboxamide (Example 37), N-(4-bromo-2,6-diethylphenyl)-2,6-dimethyl-4-propoxy-3-pyridinecarboxamide (Example 38), 6-methyl-N,2-diphenyl-4-propoxy-3-pyridinecarboxamide (Example 39), 6-methyl-N-(2,3-dimethylphenyl)-2-phenyl-4-propoxy-3-pyridinecarboxamide (Example 40), N-(2,6-diethylphenyl)-6-methyl-2-phenyl-4-propoxy-3-pyridinecarboxamide (Example 41), N-(4-bromo-2,6-diethylphenyl)-4-butoxy-2,6-dimethyl-3-pyridinecarboxamide (Example 42), 2-ethyl-N-(2,6-diethylphenyl)-6-methyl-4-propoxy-3-pyridinecarboxamide (Example 43), 5-bromo-N-(4-bromo-2,6-diethylphenyl)-2,6-dimethyl-4-propoxy-3-pyridinecarboxamide (Example 44), N-(2,6-diethylphenyl)-2,5,6-trimethyl-4-propoxy-3-pyridinecarboxamide (Example 45), 4-butoxy-2,5,6-trimethyl-N-phenyl-3-pyridinecarboxamide (Example 46), 2,6-diethyl-N-(2,6-diethylphenyl)-4-propoxy-3-pyridinecarboxamide (Example 47), N-(2,6-diethylphenyl)-2-methyl-6-phenyl-4-propoxy-3-pyridinecarboxamide (Example 48), N-(2,6-diethylphenyl)-5,6,7,8-tetrahydro-2-methyl-4-propoxy-3-quinolinecarboxamide (Example 49), 6-butyl-N-(2,6-diethylphenyl)-2-methyl-4-propoxy-3-pyridinecarboxamide (Example 50),

EXAMPLE 51

2,6-Dimethyl-N-phenyl-4-propoxy-3-pyridinecarboxamide 1-oxide

A mixture of 2.42 g (10 m mol) of 1,4-dihydro-2,6-dimethyl-4-oxo-N-phenyl-3-pyridinecarboxamide, 1.84 g (15 m mol) of n-propyl bromide, 1.52 g (11 m mol) of potassium carbonate and 40 ml of N,N-dimethylformamide was stirred for 7 hours at 90° C. (bath temperature). About 100 ml of water was added to the reaction mixture. The mixture was cooled to room temperature to precipitate crystals. The crystals were filtered off, washed and dried under reduced pressure to obtain 2.14 g of 2,6-dimethyl-N-phenyl-4-propoxy-3-pyridinecarboxamide Yield: 75.3%)

m.p.: 129°–131° C.

Then a mixture of 1.42 g (5 m mol) of 2,6-dimethyl-N-phenyl-4-propoxy-3-pyridinecarboxamide obtained thus, 2.16 g (10 m mol) of a commercially available m-chloroperbenzoic acid (80% purity) and 40 ml of chloroform was stirred for 8 hours at room temperature. The reaction mixture was discharged to a separation funnel and after the addition of the 10% aqueous sodium hydrogen sulfite solution, was shaken. The separated oil phase was washed with aqueous saturated sodium hydrogen carbonate solution and then with aqueous saturated sodium chloride solution. It was then dehydrated over anhydrous magnesium sulfate and filtered. After the filtrate was concentrated, the residue was crystallized from a mixture of ethyl acetate and hexane to obtain 1.37 g of the title compound
(Yield: 91.2%).
m.p.: 185°–186° C.

EXAMPLES 52–90

The following compounds were obtained from the corresponding 4-substitutedoxy-3-pyridinecarboxamide compounds, which were obtained by the reaction of the corresponding 1,4-dihydro-4-oxo-3-pyridinecarboxamide compounds with halogenated compounds, in a similar method to Example 51.

4-butoxy-2,6-dimethyl-N-phenyl-3-pyridinecarboxamide 1-oxide (Example 52), 2,6-dimethyl-N-(2-methylphenyl)-4-propoxy-3-pyridinecarboxamide 1-oxide (Example 53), 2,6-dimethyl-N-(2,6-dimethylphenyl)-4-propoxy-3-pyridinecarboxamide 1-oxide (Example 54), 4-butoxy-2,6-dimethyl-N-(2,3-dimethylphenyl)-3-pyridinecarboxamide 1-oxide (Example 55), 4-isobutoxy-2,6-dimethyl-N-(2,3-dimethylphenyl)-3-pyridinecarboxamide 1-oxide (Example 56), 2,6-dimethyl-N-(2,3-dimethylphenyl)-4-pentyloxy-3-pyridinecarboxamide 1-oxide (Example 57), 4-isopentyloxy-2,6-dimethyl-N-(2,3-dimethylphenyl)-3-pyridinecarboxamide 1-oxide (Example 58), 4-hexyloxy-2,6-dimethyl-N-(2,3-dimethylphenyl)-3-pyridinecarboxamide 1-oxide (Example 59), 2,6-dimethyl-N-(2,3-dimethylphenyl)-4-octyloxy-3-pyridinecarboxamide 1-oxide (Example 60), 4-(2-ethoxyethoxy)-2,6-dimethyl-N-(2,3-dimethylphenyl)-3-pyridinecarboxamide 1-oxide (Example 61), 4-allyloxy-2,6-dimethyl-N-(2,3-dimethylphenyl)-3-pyridinecarboxamide 1-oxide (Example 62), 2,6-dimethyl-N-(2,4-dimethylphenyl)-4-propoxy-3-pyridinecarboxamide 1-oxide (Example 63), 4-ethoxy-N-(2,6-diethylphenyl)-2,6-dimethyl-3-pyridinecarboxamide 1-oxide (Example 64), N-(2,6-diethylphenyl)-2,6-dimethyl-4-propoxy-3-pyridinecarboxamide 1-oxide (Example 65), N-(2,6-diethylphenyl)-4-isopropoxy-2,6-dimethyl-3-pyridinecarboxamide 1-oxide (Example 66), 4-butoxy-N-(2,6-diethylphenyl)-2,6-dimethyl-3-pyridinecarboxamide 1-oxide (Example 67), N-(2,6-diethylphenyl)-4-isobutoxy-2,6-dimethyl-3-pyridinecarboxamide 1-oxide (Example 68), N-(2,6-diethylphenyl)-2,6-dimethyl-4-pentyloxy-3-pyridinecarboxamide 1-oxide (Example 69), 4-benzyloxy-N-(2,6-diethylphenyl)-2,6-dimethyl-3-pyridinecarboxamide 1-oxide (Example 70), 4-ethoxycarbonylmethoxy-N-(2,6-diethylphenyl)-2,6-dimethyl-3-pyridinecarboxamide 1-oxide (Example 71), 4-(1-ethoxycarbonylethoxy)-N-(2,6-dimethylphenyl)-2,6-dimethyl-3-pyridinecarboxamide 1-oxide (Example 72), N-(2-methoxyphenyl)-2,6-dimethyl-4-propoxy-3-pyridinecarboxamide 1-oxide (Example 73), 2,6-dimethyl-N-(3-nitrophenyl)-4-propoxy-3-pyridinecarboxamide 1-oxide (Example 74), 6-methyl-N,2-diphenyl-4-propoxy-3-pyridinecarboxamide 1-oxide (Example 75), 5-bromo-N-(2,6-diethylphenyl)-2,6-dimethyl-4-propoxy-3-pyridinecarboxamide 1-oxide (Example 76), 6-methyl-N-(2,3-dimethylphenyl)-2-phenyl-4-propoxy-3-pyridinecarboxamide 1-oxide (Example 77), N-(2,6-diethylphenyl)-6-methyl-2-phenyl-4-propoxy-3-pyridinecarboxamide 1-oxide (Example 78), 4-cyclohexylmethoxy-2,6-dimethyl-N-(2,3-dimethylphenyl)-3-pyridinecarboxamide 1-oxide (Example 79), 4-(2-chloroethoxy)-2,6-dimethyl-N-(2,3-dimethylphenyl)-3-pyridinecarboxamide 1-oxide (Example 80), N-(4-bromo-2,6-diethylphenyl)-2,6-dimethyl-4-propoxy-3-pyridinecarboxamide 1-oxide (Example 81), N-(2,6-diethylphenyl)-2,6-dimethyl-4-(2-phenylethyloxy)-3-pyridinecarboxamide 1-oxide (Example 82), 5-bromo-N-(4-bromo-2,6-diethylphenyl)-2,6-dimethyl-4-propoxy-3-pyridinecarboxamide 1-oxide (Example 83), 2-ethyl-N-(2,6-diethylphenyl)-6-methyl-4-propoxy-3-pyridinecarboxamide 1-oxide (Example 84), N-(2,6-diethylphenyl)-2,5,6-trimethyl-4-propoxy-3-pyridinecarboxamide 1-oxide (Example 85), 2,6-diethyl-N-(2,6-diethylphenyl)-4-propoxy-3-pyridinecarboxamide 1-oxide (Example 86), 4-butoxy-2,5,6-trimethyl-N-phenyl-3-pyridinecarboxamide 1-oxide (Example 87), 6-butyl-N-(2,6-diethylphenyl)-2-methyl-4-propoxy-3-pyridinecarboxamide 1-oxide (Example 88), N-(2,6-diethylphenyl)-5,6,7,8-tetrahydro-2-methyl-4-propoxy-3-quinolinecarboxamide 1-oxide (Example 89), N-(2,6-diethylphenyl)-4-isobutoxy-5,6-dimethyl-2-propyl-3-pyridinecarboxamide 1-oxide (Example 90),

REFERENCE EXAMPLE

A carrier was prepared by mixing 50 parts (by weight) of talc, 25 parts of bentonite, 2 parts of "Solpole-9047" (Toho Chemical Co., Ltd, Japan) and 3 parts of "Solpole-5039" (Toho Chemical Co., Ltd, Japan). 50 parts of a test compound and 200 parts of the carrier were mixed to obtain 20% wettable powder, followed by dispersing the powder in distilled water to make a dispersion of the definite concentrations.

Seeds of *Oryza sativa* L., *Echinochloa crus-galli* L., and *Raphanus sativus* L., were germinated in a laboratory dish, to which the dispersion was added. After breeding for 7 days in a thermostatic box kept at 25° C. under illumination of fluorescent tubes, growth of plant was observed. In the column of "Evaluation" of Table 2, the designation 1 denotes no influence, 2 denotes 25% growth inhibition, 3 denotes 50% growth inhibition, 4 denotes 75% growth inhibition and 5 denotes 100% growth inhibition.

TABLE 1

| Example No. | R' | Y | NMR (CDCl₃) δ-value | IR(KBr) cm⁻¹ | m.p. (°C.) |
|---|---|---|---|---|---|
| 1 | n-butyl | bromide | 0.60–2.20(m, 7H), 1.23(t, 6H), 2.50(s, 3H), 2.63(s, 3H), 2.75(q, 4H), 4.07(t, 2H), 6.56(s, 1H), 6.80–7.40(m, 4H) | 1643 | 143–145 |
| 2 | ethyl | iodide | 1.41(t, 3H), 2.48(s, 3H), 2.56(s, 3H), 4.10(q, 2H), 6.52(s, 1H), 6.65–7.77(m, 5H), 7.91(br, 1H) | 1663 | 1335–1355 |

TABLE 1-continued

| | | | | |
|---|---|---|---|---|
| 3 | allyl bromide | 2.32(s, 3H), 2.49(s, 3H), 4.54(d, 2H), 5.04–5.54(m, 2H), 5.59–6.29(m, 1H), 6.46(s, 1H), 6.89–7.79(m, 5H), 8.42(br, 1H) | 1647 | foaming |
| 4 | benzyl bromide | 2.46(s, 3H), 2.57(s, 3H), 5.10(s, 2H), 6.60(s, 1H), 6.75–7.80(m, 10H), 7.97(br, 1H) | 1642 | 172–174 |
| 5 | methyl α-bromoacetate | 2.46(s, 3H), 2.58(s, 3H), 3.77(s, 3H), 4.73(s, 2H), 6.43(s, 1H), 6.80–7.80(m, 5H), 8.58(br, 1H) | 1672, 1748 | 129–132 |
| 6 | n-propyl bromide | 1.01(t, 3H), 1.21(t, 6H), 1.40–2.20(m, 2H), 2.48(s, 3H), 2.60(s, 3H), 2.72(q, 4H), 4.00(t, 2H), 6.51(s, 1H), 6.80–7.30(m, 4H) | 1637 | 154–157 |
| 7 | benzyl bromide | 1.06(t, 6H), 2.50(s, 3H), 2.57(q, 4H), 2.66(s, 3H), 5.13(s, 2H), 6.62(s, 1H), 6.80–7.50(m, 9H) | 1633 | 179–181 |
| 8 | phenetyl bromide | 1.20(t, 6H), 2.49(s, 3H), 2.63(s, 3H), 2.67(q, 4H), 3.12 (t, 2H), 4.31(t, 2H), 6.57(s, 1H), 6.80–7.50(m, 9H) | 1642 | 166–169 |
| 9 | n-butyl bromide | 0.60–2.30(m, 7H), 1.23(t, 6H), 2.62(s, 3H), 2.65(s, 3H), 2.74(q, 4H), 4.06(t, 2H), 6.80–7.30(m, 4H) | 1640 | 184–1855 |
| 10 | n-propyl bromide | 0.97(t, 3H), 1.40–2.20(m, 2H), 2.48(s, 3H), 2.58(s, 3H), 3.98(t, 2H), 6.53(s, 1H), 6.70–8.70(m, 5H) | 1677 | 111.5–113.5 |
| 11 | n-propyl bromide | 1.01(t, 3H), 1.40–2.20(m, 2H), 2.21(s, 3H), 2.30(s, 3H), 2.48 (s, 3H), 2.59(s, 3H), 4.00(t, 2H), 6.54(s, 1H), 6.97–7.80(m, 4H) | 1673 | 163–166 |
| 12 | n-propyl bromide | 0.94(t, 3H), 1.73(six, 2H), 2.41(s, 3H), 2.46(s, 3H), 3.88(t, 2H), 6.38(s, 1H), 6.80–7.85(m, 5H), 8.48(s, 1H) | 1670 | 129–131 |
| 13 | n-butyl bromide | 0.60–2.30(m, 7H), 2.45(s, 3H), 2.51(s, 3H), 3.97(t, 2H), 6.45(s, 1H), 6.85–8.00(m, 5H), 8.33(s, 1H) | 1667 | 110–112 |
| 14 | n-propyl bromide | 1.00(t, 3H), 1.82(six, 2H), 2.28(s, 3H), 2.48(s, 3H), 2.57(s, 3H), 3.99(t, 2H), 6.53(s, 1H), 6.85–8.00(m, 4H), 7.45(s, 1H) | 1638 | 137–137.5 |
| 15 | ethyl iodide | 1.42(t, 3H), 2.20(s, 3H), 2.28(s, 3H), 2.47(s, 3H), 2.57(s, 3H), 4.08(q, 2H), 6.47(s, 1H), 6.80–7.60(m, 3H), 7.33(s, 1H) | 1662 | 184–187 |
| 16 | n-butyl bromide | 0.60–2.10(m, 7H), 2.19(s, 3H), 2.28(s, 3H), 2.48(s, 3H), 2.57(s, 3H), 4.00(t, 2H), 6.50(s, 1H), 6.80–7.60(m, 4H) | 1645 | 132–134 |
| 17 | isobutyl bromide | 1.00(d, 6H), 1.70–2.40(m, 1H), 2.20(s, 3H), 2.30(s, 3H), 2.48(s, 3H), 2.58(s, 3H), 3.79(d, 2H), 6.50(s, 1H), 6.85–7.60(m, 4H) | 1650 | 148–149 |
| 18 | n-amyl bromide | 0.60–2.15(m, 9H), 2.20(s, 3H), 2.29(s, 3H), 2.47(s, 3H), 2.57(s, 3H), 4.00(t, 2H), 6.50(s, 1H), 6.80–7.70(m, 4H) | 1645 | 133.5–135 |
| 19 | isoamyl bromide | 0.92(d, 6H), 1.30–2.10(m, 3H), 2.17(s, 3H), 2.27(s, 3H), 2.44(s, 3H), 2.52(s, 3H), 4.00(t, 2H), 6.48(s, 1H), 6.80–7.55(m, 3H), 7.70(s, 1H) | 1640 | 132–134 |
| 20 | n-hexyl bromide | 0.60–2.10(m, 11H), 2.18(s, 3H), 2.28(s, 3H), 2.46(s, 3H), 2.55(s, 3H), 3.99(t, 2H), 6.49(s, 1H), 6.95–7.70(m, 3H), 7.50(s, 1H) | 1648, 1670 | 125–127 |
| 21 | n-octyl bromide | 0.60–2.10(m, 15H), 2.16(s, 3H), 2.26(s, 3H), 2.43(s, 3H), 2.50(s, 3H), 3.95(t, 2H), 6.47(s, 1H), 6.70–7.60(m, 3H), 7.87(s, 1H) | 1645 | 139–141 |
| 22 | allyl bromide | 2.17(s, 3H), 2.27(s, 3H), 2.47(s, 3H), 2.58(s, 3H), 4.57(d, 2H), 5.05–5.60(m, 2H), 5.60–6.40(m, 1H), 6.50(s, 1H), 6.80–7.70(m, 4H) | 1640, 1653 | 148–151 |
| 23 | propargyl bromide | 2.23(s, 3H), 2.31(s, 3H), 2.53(s, 3H), 2.57(t, 1H), 2.62(s, 3H), 4.75(d, 2H), 6.67(s, 1H), 6.90–7.90(m, 4H) | 1643 | 180.5–182 |
| 24 | β-phenetyl bromide | 2.09(s, 3H), 2.28(s, 3H), 2.45(s, 3H), 2.54(s, 3H), 3.05(t, 2H), 4.22(t, 2H), 6.49(s, 1H), 6.60–7.60(m, 9H) | 1640 | 152–157 |
| 25 | cyclohexyl-methyl bromide | 0.50–2.10(m, 11H), 2.18(s, 3H), 2.27(s, 3H), 2.43(s, 3H), 2.53(s, 3H), 3.76(d, 2H), 6.46(s, 1H), 6.70–7.60(m, 3H), 7.80(s, 1H) | 1648 | 164–167 |
| 26 | n-propyl bromide | 1.00(t, 3H), 1.83(six, 2H), 2.33(s, 6H), 2.48(s, 3H), 2.60(s, 3H), 4.00(t, 2H), 6.55(s, 1H), 7.08(s, 3H), 7.24(s, 1H) | 1640 | 166–169 |
| 27 | ethyl iodide | 1.21(t, 6H), 1.43(t, 3H), 2.47(s, 3H), 2.59(s, 3H), 2.73(q, 4H), 4.11(q, 2H), 6.54(s, 1H), 6.90–7.50(m, 4H) | 1640 | 180–183 |
| 28 | isopropyl iodide | 1.20(t, 6H), 1.36(d, 6H), 2.44(s, 3H), 2.56(s, 3H), 2.70(q, 4H), 4.63(sep, 1H), 6.49(s, 1H), 6.90–7.40(m, 3H), 7.17(s, 1H) | 1638 | 171–175.5 |
| 29 | isobutyl bromide | 0.99(d, 6H), 1.20(t, 6H), 1.70–2.50(m, 1H), 2.46(s, 3H), 2.57(s, 3H), 2.71(q, 4H), 3.79(d, 2H), 6.52(s, 1H), 6.90–7.50(m, 3H), 7.26(s, 1H) | 1635 | 164–165 |
| 30 | n-amyl bromide | 0.60–2.20(m, 9H), 1.22(t, 6H), 2.48(s, 3H), 2.60(s, 3H), 4.04(t, 2H), 6.55(s, 1H), 6.90–7.50(m, 4H) | 1635 | 143–145 |
| 31 | ethyl bromo-acetate | 1.20(t, 6H), 1.23(t, 3H), 2.47(s, 3H), 2.65(s, 3H), 2.71(q, 4H), 4.18(q, 2H), 4.73(s, 2H), 6.47(s, 1H), 7.00–7.30(m, 3H), 7.96(s, 1H) | 1640, 1745, 1770 | 157–159 |
| 32 | ethyl α-bromo-propionate | 1.23(t, 9H), 1.66(d, 3H), 2.46(s, 3H), 2.64(s, 3H), 2.75(q, 4H), 4.17(q, 2H), 4.98(q, 1H), 6.45(s, 1H), 7.00–7.30(m, 3H), 8.01(s, 1H) | 1638, 1732 | 156.5–159 |
| 33 | n-propyl | 0.97(t, 3H), 1.21(t, 6H), 1.79(six, 2H), | 1640 | 172–177 |

TABLE 1-continued

| | | | | |
|---|---|---|---|---|
| | bromide | 2.57(s, 3H), 2.63(s, 3H), 2.70(q, 4H), 4.00(t, 2H), 7.00-7.30(m, 3H), 7.35(s, 1H) | | |
| 34 | n-propyl bromide | 0.94(t, 3H), 1.76(six, 2H), 2.47(s, 3H), 2.57(s, 3H), 3.78(s, 3H), 3.97(t, 2H), 6.55(s, 1H), 6.60-8.70(m, 4H), 8.23(s, 1H) | 1670 | 120-122 |
| 35 | n-propyl bromide | 0.96(t, 3H), 1.78(six, 2H), 2.43(s, 3H), 2.46(s, 3H), 3.96(t, 2H), 6.46(s, 1H), 7.25-8.65(m, 4H), 9.04(s, 1H) | 1657 | 152-153 |
| 36 | 2-bromoethyl ethyl ether | 1.05(t, 3H), 2.17(s, 3H), 2.26(s, 3H), 2.43(s, 3H), 2.52(s, 3H), 3.43(q, 2H), 3.50-3.90(m, 2H), 3.90-4.30(m, 2H), 6.47(s, 1H), 6.80-7.50(m, 3H), 8.07(s, 1H) | 1645 | 126.5-128 |
| 37 | 1-bromo-2-chloroethane | 2.21(s, 3H), 2.27(s, 3H), 2.48(s, 3H), 2.59(s, 3H), 3.77(t, 2H), 4.27(t, 2H), 6.49(s, 1H), 6.80-7.60(m, 4H) | 1645 | 123-125 |
| 38 | n-propyl bromide | 1.00(t, 3H), 1.20(t, 6H), 1.82(six, 2H), 2.47(s, 3H), 2.59(s, 3H), 2.67(q, 4H), 3.99(t, 2H), 6.50(s, 1H), 7.00(br, 1H), 7.18(s, 2H) | 1643 | 202-205.5 |
| 39 | n-propyl bromide | 0.97(t, 3H), 1.76(six, 2H), 2.58(s, 3H), 3.97(t, 2H), 6.62(s, 1H), 6.80-8.10(m, 11H) | 1645 | 143.5-146 |
| 40 | n-propyl bromide | 0.99(t, 3H), 1.20-2.30(m, 2H), 1.80(s, 3H), 2.17(s, 3H), 2.53(s, 3H), 3.95(t, 2H), 6.57(s, 1H), 6.70-7.85(m, 9H) | 1645 | 165-169 |
| 41 | n-propyl bromide | 0.95(t, 6H), 1.01(t, 3H), 1.81(six, 2H), 2.16(q, 4H), 2.56(s, 3H), 3.97(t, 2H), 6.64(s, 1H), 6.80-7.90(m, 9H) | 1637 | 214-216 |
| 42 | n-butyl bromide | 0.60-2.20(m, 7H), 1.23(t, 6H), 2.52(s, 3H), 2.63(s, 3H), 2.74(q, 4H), 4.10(t, 2H), 6.58(s, 1H), 7.02(br, 1H), 7.10-7.35(m, 2H) | 1647 | |
| 43 | n-propyl bromide | 1.00(t, 3H), 1.23(t, 6H), 1.81(t, 3H), 1.79(six, 2H), 2.50(s, 3H), 2.75(q, 4H), 2.89(q, 2H), 4.00(t, 2H), 6.51(s, 1H), 6.90-7.25(m, 4H) | 1647 | |
| 44 | n-propyl bromide | | 1645 | |
| 45 | n-propyl bromide | 0.96(t, 3H), 1.23(t, 6H), 1.79(six, 2H), 2.19(s, 1H), 2.47(s, 3H), 2.61(s, 3H), 2.74(q, 4H), 3.85(t, 2H), 6.90-7.30(m, 4H) | 1647 | 150-152 |
| 46 | n-butyl bromide | 0.60-2.25(m, 7H), 2.10(s, 3H), 2.41(s, 3H), 2.47(s, 3H), 3.88(t, 2H) 6.80-7.90(m, 5H), 8.33(br, 1H) | 1673 | 102-106 |
| 47 | n-propyl bromide | 1.00(t, 3H), 1.23(t, 6H), 1.34(t, 6H), 1.84(six, 2H), 2.76(q, 6H), 2.92(q, 2H), 4.01(t, 2H), 6.52(s, 1H), 6.90-7.40(m, 4H) | 1640 | 210-213 |
| 48 | n-propyl bromide | 1.01(t, 3H), 1.21(t, 6H), 1.86(six, 2H), 2.68(s, 3H), 2.73(q, 4H), 4.05(t, 2H), 6.80-8.15(m, 10H) | 1650 | 172-176 |
| 49 | n-propyl bromide | 0.70-1.45(m, 9H), 1.45-2.20(m, 6H), 2.20-3.10(m, 11H), 3.87(t, 2H) 6.90-7.30(m, 4H) | 1665 (neat) | |
| 50 | n-propyl bromide | 0.60-2.35(m, 12H), 1.21(t, 6H), 2.40-3.20(m, 6H), 2.60(s, 3H), 3.99(t, 2H), 6.50(s, 1H), 6.90-7.40(m, 4H) | 1643 | 100-103 |

| Example No. | N M R (C D C l₃*) δ-value | IR(KBr) $\nu c=o$ (cm$^{-1}$) | m.p. (°C.) |
|---|---|---|---|
| 51 | 0.98(t, 3H), 1.77(six, 2H), 2.38(s, 6H), 3.93(t, 2H), 6.46(s, 1H), 6.90-8.10(m, 5H), 11.10(s, 1H) | 1660 | 185-186 |
| 52 | 0.60-2.20(m, 7H), 2.86(s, 6H), 3.95(t, 2H), 6.43(s, 1H), 6.85-8.00(m, 5H), 10, 84(s, 1H) | 1662 | 201-201.5 |
| 53 | 1.04(t, 3H), 1.78(six, 2H), 2.42(s, 6H), 2.51(s, 3H), 3.97(t, 2H), 6.56(s, 1H), 7.00-7.80(m, 4H), 9.60(s, 1H) | 1660 | 245-246 |
| 54 | | 1663 | 264-265.5 |
| 55 | 0.60-2.20(m, 7H), 2.29(s, 3H), 2.33(s, 3H), 2.47(s, 3H), 2.56(s, 3H), 4.06(t, 2H), 6.75(s, 1H), 6.95-7.60(m, 3H), 9.85(s, 1H) | 1660 | 253-255 |
| 56 | 1.03(d, 6H), 1.70-2.60(m, 1H), 2.30(s, 6H), 2.34(s, 3H), 2.48(s, 3H), 3.73(d, 2H), 6.46(s, 1H), 6.85-7.50(m, 3H), 9.86(s, 1H) | 1667 | 258-259.5 |
| 57 | 0.60-2.20(m, 9H), 2.31(s, 6H), 2.39(s, 3H), 2.51(s, 3H), 4.03(t, 2H), 6.57(s, 1H), 7.00-7.60(m, 3H), 9.69(s, 1H) | 1660 | 211-213 |
| 58 | | 1662 | 224-226 |
| 59 | 0.60-2.15(m, 11H), 2.30(s, 6H), 2.36(s, 3H), 2.48(s, 3H), 3.97(t, 2H), 6.50(s, 1H), 6.95-7.50(m, 3H), 9.89(s, 1H) | 1665 | 230-231 |
| 60 | 0.60-2.15(m, 15H), 2.30(s, 6H), 2.33(s, 3H), 2.47(s, 3H), 3.93(t, 2H), 6.45(s, 1H), 6.90-7.50(m, 3H), 9.99(s, 1H) | 1660 | 199-201.5 |
| 61 | 1.15(t, 3H), 2.30(s, 6H), 2.40(s, 3H), 2.53(s, 3H), 3.52(q, 2H), 3.60-3.90(m, 2H), 4.00-4.35(m, 2H), 6.60(s, 1H), 6.90-7.50(m, 3H), 9.68(s, 1H) | 1660 | 187.5-189 |
| 62 | 2.25(s, 3H), 2.30(s, 3H), 2.45(s, 3H), 2.53(s, 3H), 4.59 (d, 2H), 5.00-6.40(m, 3H), 6.61(s, 1H), 6.90-7.60(m, 3H), 8.60(s, 1H) | 1662 | 228.5-231 |
| 63 | 1.03(t, 3H), 1.86(six, 2H), 2.43(s, 9H), 2.60(s, 3H), 3.97(t, 2H), 6.54(s, 1H), 7.09(s, 3H), 9.50(s, 1H) | 1648 | 2375-238.5 |
| 64 | 1.26(t, 6H), 1.44(t, 3H), 2.34(s, 3H), 2.56(s, 3H), 2.79 (q, 4H), 4.03(q, 2H), 6.48(s, 1H), 6.90-7.40(m, 3H), 9.72(s, 1H) | 1645 | 218-218.5 |
| 65 | 1.03(t, 3H), 1.28(t, 6H), 186(six, 2H), 2.37(s, 3H), 2.59(s, 3H), 2.82(q, 4H), 3.95(t, 2H), 6.49(s, 1H), 6.90-7.30(m, 3H), 9.58(s, 1H) | 1645 | 233-234 |
| 66 | 1.28(t, 6H), 1.33(d, 6H), 2.34(s, 3H), 2.54(s, 3H), 2.81 (q, 4H), 4.51(sep, 1H), 6.49(s, 1H), 7.10(s, 3H), 9.90(s, 1H) | 1645 | 111-115 |
| 67 | 0.60-2.20(m, 7H), 1.27(t, 6H), 2.36(s, 3H), 2.57(s, 3H), 2.81(q, 4H), 4.00(t, 2H), 6.52(s, 1H), 6.90-7.40(m, 3H), 9.75(s, 1H) | 1645 | 215-216 |
| 68 | 1.03(d, 5H), 1.29(t, 6H), 1.70-2.60(m, 1H), 2.36(s, 3H), 2.59(s, 3H), 2.83(q, 4H), 3.76(d, 2H), 6.47(s, 1H), 6.90-7.40(m, 3H), 9.83(s, 1H) | 1670 | 158-159.5 |
| 69 | 0.60-2.20(m, 9H), 1.28(t, 6H), 2.34(s, 3H), 2.57(s, 3H), 2.81(q, 4H), 3.97(t, 2H), 6.47(s, 1H), 7.00-7.30(m, 3H), 9.78(s, 1H) | 1662 | 182-184.5 |
| 70 | 1.10(t, 6H), 2.44(s, 3H), 2.64(s, 3H), 2.66(q, 4H), 5.14(s, 2H), 6.72(s, 1H), 6.90-7.80(m, 8H), 9.20(s, 1H) | 1652 | 199-201 |
| 71 | 1.23(t, 6H), 1.26(t, 3H), 2.44(s, 3H), 2.62(s, 3H), 2.74(q, 4H), 4.20 (q, 2H), 4.72(s, 2H), 6.64(s, 1H), 7.00-7.40(m, 3H), 8.87(s, 1H) | 1645 1767 | 204.5-207 |
| 72 | 1.25(t, 9H), 1.64(d, 3H), 2.44(s, 3H), 2.62(s, 3H), 2.79(q, | 1643 | 165-167. |

TABLE 1-continued

| | | | |
|---|---|---|---|
| | 4H), 4.19(q, 2H), 4.89(q, 1H), 6.63(s, 1H), 7.03-7.40(m, 3H), 9.13(s, 1H) | 1772 | |
| 73 | 0.96(t, 3H), 1.77(six, 2H), 2.50(s, 3H), 2.58(s, 3H), 3.81(s, 3H), 3.97(t, 3H), 6.68(s, 1H), 6.70-8.60(m, 4H), 8.44(s, 1H) | 1667 | 195-197 |
| 74 | 0.98(t, 3H), 1.80(six, 2H), 2.40(s, 6H), 3.98(t, 2H), 6.57(s, 1H), 7.30-9.00(m, 4H), 11.73(s, 1H) | 1672 | 217.5-219 |
| 75 | 0.95(t, 3H), 1.75(six, 2H), 2.43(s, 3H), 3.93(t, 2H), 6.71(s, 1H), 6.80-8.00(m, 10H), 8.49(s, 1H) | 1650 | 191-195 |
| 76 | 1.00(t, 3H), 1.32(t, 6H), 1.84(six, 2H), 2.55(s, 3H), 2.61(s, 3H), 2.85(q, 4H), 4.01(t, 2H), 7.16(s, 3H), 9.88(s, 1H) | 1675 | 148-152 |
| 77 | 0.97(t, 3H), 1.40-2.20(m, 2H), 1.70(s, 3H), 2.13(s, 3H), 2.37(s, 3H), 3.87(t, 2H), 6.25-7.80(m, 9H), 8.03(s, 1H) | 1645 | 226-227 |
| 78 | 0.94(t, 6H), 1.01(t, 3H), 1.80(six, 6H), 2.44(s, 3H), 3.96(t, 2H), 6.60-8.00(m, 10H) | 1642 | 240-242 |
| 79 | 0.80-2.20(m, 11H), 2.22(s, 3H), 2.28(s, 3H), 2.55(s, 6H), 3.92(d, 2H), 4.68(s, 1H), 6.90-7.30(m, 4H) | 1662 | 250-254 |
| 80 | | 1650 1660 | 187.5-191 |
| 81 | 1.01(t, 3H), 1.24(t, 6H), 1.83(six, 2H), 2.30(s, 3H), 2.50(s, 3H), 2.75(q, 4H), 3.92(t, 2H), 6.43(s, 1H), 7.18(s, 2H), 9.89(s, 1H) | 1645 | 265-268 |
| 82 | | 1645 | 202-203 |
| 83 | | 1687 | 228.5-230 |
| 84 | 1.03(t, 3H), 1.23(t, 3H), 1.29(t, 6H), 1.87(six, 2H), 2.40(s, 3H), 2.84(q, 4H), 3.10(q, 2H), 3.94(t, 2H), 6.48(s, 1H), 7.00-7.40(m, 3H) 9.50(s, 1H) | 1665 | 178-181 |
| 85 | 0.97(t, 3H), 1.33(t, 6H), 1.79(six, 2H), 2.18(s, 3H), 2.35(s, 3H), 2.56(s, 3H), 2.88(q, 4H), 3.85(t, 2H), 7.00-7.30(m, 3H), 10.10(s, 1H) | 1680 | 175-177 |
| 86 | 1.03(t, 3H), 1.21(t, 6H), 1.28(t, 6H), 1.86(six, 2H), 2.79(q, 2H), 2.82(q, 4H), 3.08(q, 2H), 3.92(t, 2H), 6.36(s, 1H), 7.00-7.20(m, 3H) 9.47(s, 1H) | 1663 | 138-140 |
| 87 | 0.60-2.25(m, 7H), 2.12(s, 3H), 2.32(s, 3H), 2.35(s, 3H), 4.00(t, 2H) 6.80-8.00(m, 5H), 11.36(br, 1H) | 1677 | 188-190 |
| 88 | 0.60-2.20(m, 12H), 1.79(t, 6H), 2.40-3.20(m, 6H), 2.58(s, 3H), 3.94(t, 2H), 6.41(s, 1H), 7.00-7.25(m, 3H), 9.66(s, 1H) | 1673 | |
| 89 | 0.98(t, 3H), 1.30(t, 6H), 1.40-2.15(m, 6H), 2.20-3.10(m, 4H), 2.59(s, 3H), 2.83(q, 4H), 3.91(t, 2H), 6.90-7.25(m, 3H), 9.68(s, 1H) | 1673 | 193-196 |
| 90 | 0.95(t, 3H), 0.97(d, 6H), 1.30-2.50(m, 3H), 1.33(t, 6H), 2.18(s, 3H), 2.37(s, 3H), 2.88(q, 4H), 3.30(t, 2H), 3.63(d, 2H), 7.13(s, 3H), 9.73(s, 1H) | 1673 | 210-214 |

*Example No. 55: CDCl$_3$—DMSO—d$_6$
Example No. 79: CD$_3$OD

| Example No. | concentration (ppm) | Plant | | | Example No. | concentration (ppm) | Plant | | |
|---|---|---|---|---|---|---|---|---|---|
| | | X | Y | Z | | | X | Y | Z |
| 1 | 20 | 4 | 4 | 4 | 18 | 20 | 5 | 5 | 5 |
| | 100 | 5 | 5 | 4 | | 100 | 5 | 5 | 5 |
| 2 | 20 | 1 | 3 | 3 | 19 | 20 | 5 | 5 | 4 |
| | 100 | 4 | 4 | 4 | | 100 | 5 | 5 | 5 |
| 3 | 20 | 1 | 4 | 4 | 20 | 20 | 4 | 5 | 4 |
| | 100 | 4 | 4 | 5 | | 100 | 5 | 5 | 4 |
| 4 | 20 | 1 | 2 | 1 | 21 | 20 | 1 | 3 | 1 |
| | 100 | 2 | 2 | 1 | | 100 | 2 | 4 | 1 |
| 5 | 20 | 1 | 1 | 1 | 22 | 20 | 4 | 5 | 4 |
| | 100 | 2 | 2 | 1 | | 100 | 4 | 5 | 5 |
| 6 | 20 | 4 | 4 | 4 | 23 | 20 | 1 | 4 | 4 |
| | 100 | 4 | 5 | 4 | | 100 | 1 | 4 | 4 |
| 7 | 20 | 3 | 3 | 4 | 24 | 20 | 2 | 2 | 1 |
| | 100 | 3 | 4 | 4 | | 100 | 3 | 3 | 4 |
| 8 | 20 | 1 | 1 | 2 | 25 | 20 | 3 | 2 | 4 |
| | 100 | 1 | 2 | 2 | | 100 | 3 | 4 | 5 |
| 9 | 20 | 1 | 4 | 2 | 26 | 20 | 4 | 4 | 4 |
| | 100 | 1 | 4 | 2 | | 100 | 4 | 4 | 4 |
| 10 | 20 | 4 | 5 | 4 | 27 | 20 | 4 | 5 | 4 |
| | 100 | 5 | 5 | 4 | | 100 | 4 | 5 | 4 |
| 11 | 20 | 4 | 5 | 4 | 28 | 20 | 1 | 4 | 4 |
| | 100 | 4 | 5 | 4 | | 100 | 2 | 5 | 4 |
| 12 | 20 | 3 | 4 | 4 | 29 | 20 | 4 | 5 | 5 |
| | 100 | 4 | 5 | 4 | | 100 | 5 | 5 | 5 |
| 13 | 20 | 2 | 4 | 4 | 30 | 20 | 4 | 4 | 4 |
| | 100 | 5 | 5 | 4 | | 100 | 5 | 5 | 4 |
| 14 | 20 | 4 | 4 | 4 | 31 | 20 | 1 | 1 | 4 |
| | 100 | 4 | 4 | 4 | | 100 | 4 | 4 | 5 |
| 15 | 20 | 2 | 4 | 4 | 32 | 20 | 1 | 2 | 3 |
| | 100 | 4 | 4 | 4 | | 100 | 4 | 4 | 4 |
| 16 | 20 | 4 | 5 | 4 | 33 | 20 | 4 | 5 | 3 |
| | 100 | 4 | 5 | 4 | | 100 | 4 | 5 | 4 |
| 17 | 20 | 4 | 5 | 4 | 34 | 20 | 2 | 5 | 5 |
| | 100 | 4 | 5 | 4 | | 100 | 5 | 5 | 5 |

| Example No. | concentration (ppm) | Plant X | Plant Y | Plant Z |
|---|---|---|---|---|
| 35 | 20 | 3 | 5 | 4 |
|  | 100 | 5 | 5 | 5 |
| 36 | 20 | 2 | 3 | 4 |
|  | 100 | 4 | 5 | 5 |
| 37 | 20 | 5 | 5 | 5 |
|  | 100 | 5 | 5 | 5 |
| 38 | 20 | — | — | — |
|  | 100 | — | — | — |
| 39 | 20 | 4 | 5 | 5 |
|  | 100 | 5 | 5 | 5 |
| 40 | 20 | 5 | 5 | 5 |
|  | 100 | 5 | 5 | 5 |
| 41 | 20 | 5 | 5 | 5 |
|  | 100 | 5 | 5 | 5 |
| 42 | 20 | 4 | 5 | 5 |
|  | 100 | 4 | 5 | 5 |
| 43 | 20 | 4 | 5 | 4 |
|  | 100 | 5 | 5 | 4 |
| 44 | 20 | — | — | — |
|  | 100 | — | — | — |
| 45 | 20 | 4 | 5 | 5 |
|  | 100 | 4 | 5 | 5 |
| 46 | 20 | 1 | 4 | 3 |
|  | 100 | 4 | 5 | 5 |
| 47 | 20 | 5 | 5 | 5 |
|  | 100 | 5 | 5 | 5 |
| 48 | 20 | 1 | 1 | 4 |
|  | 100 | 2 | 1 | 4 |
| 49 | 20 | 5 | 5 | 4 |
|  | 100 | 5 | 5 | 4 |
| 50 | 20 | 3 | 5 | 4 |
|  | 100 | 3 | 5 | 4 |
| 51 | 20 | 1 | 3 | 4 |
|  | 100 | 4 | 4 | 4 |
| 52 | 20 | 1 | 2 | 4 |
|  | 100 | 3 | 4 | 4 |
| 53 | 20 | 1 | 4 | 4 |
|  | 100 | 4 | 4 | 4 |
| 54 | 20 | 4 | 4 | 5 |
|  | 100 | 5 | 5 | 5 |
| 55 | 20 | 3 | 4 | 4 |
|  | 100 | 4 | 5 | 4 |
| 56 | 20 | 4 | 5 | 4 |
|  | 100 | 5 | 5 | 4 |
| 57 | 20 | 4 | 5 | 4 |
|  | 100 | 5 | 5 | 4 |
| 58 | 20 | 3 | 4 | 5 |
|  | 100 | 4 | 4 | 5 |
| 59 | 20 | 1 | 3 | 4 |
|  | 100 | 1 | 3 | 4 |
| 60 | 20 | 1 | 1 | 1 |
|  | 100 | 1 | 1 | 1 |
| 61 | 20 | 1 | 1 | 4 |
|  | 100 | 4 | 4 | 4 |
| 62 | 20 | 4 | 5 | 5 |
|  | 100 | 5 | 5 | 5 |
| 63 | 20 | 1 | 4 | 4 |
|  | 100 | 4 | 4 | 4 |
| 64 | 20 | 4 | 4 | 4 |
|  | 100 | 5 | 5 | 4 |
| 65 | 20 | 4 | 4 | 4 |
|  | 100 | 4 | 5 | 4 |
| 66 | 20 | 5 | 5 | 5 |
|  | 100 | 5 | 5 | 5 |
| 67 | 20 | 4 | 4 | 4 |
|  | 100 | 5 | 5 | 5 |
| 68 | 20 | 4 | 4 | 4 |
|  | 100 | 5 | 5 | 4 |
| 69 | 20 | 2 | 4 | 4 |
|  | 100 | 4 | 4 | 4 |
| 70 | 20 | 1 | 1 | 4 |
|  | 100 | 3 | 4 | 4 |
| 71 | 20 | 1 | 1 | 3 |
|  | 100 | 1 | 1 | 5 |
| 72 | 20 | 1 | 3 | 1 |
|  | 100 | 1 | 3 | 5 |
| 73 | 20 | 2 | 4 | 4 |
|  | 100 | 3 | 4 | 5 |
| 74 | 20 | 2 | 5 | 5 |
|  | 100 | 5 | 5 | 5 |
| 75 | 20 | 4 | 5 | 5 |
|  | 100 | 4 | 5 | 5 |
| 76 | 20 | 5 | 5 | 5 |
|  | 100 | 5 | 5 | 5 |
| 77 | 20 | 4 | 4 | 5 |
|  | 100 | 4 | 5 | 5 |
| 78 | 20 | 4 | 5 | 4 |
|  | 100 | 5 | 5 | 4 |
| 79 | 20 | 2 | 1 | 4 |
|  | 100 | 3 | 3 | 4 |
| 80 | 20 | 4 | 3 | 5 |
|  | 100 | 4 | 4 | 5 |
| 81 | 20 | 4 | 5 | 5 |
|  | 100 | 5 | 5 | 5 |
| 82 | 20 | — | — | — |
|  | 100 | — | — | — |
| 83 | 20 | 5 | 5 | 5 |
|  | 100 | 5 | 5 | 5 |
| 84 | 20 | 2 | 5 | 5 |
|  | 100 | 5 | 5 | 5 |
| 85 | 20 | 4 | 4 | 5 |
|  | 100 | 5 | 5 | 5 |
| 86 | 20 | 5 | 5 | 5 |
|  | 100 | 5 | 5 | 5 |
| 87 | 20 | 1 | 1 | 3 |
|  | 100 | 1 | 3 | 4 |
| 88 | 20 | 1 | 4 | 5 |
|  | 100 | 4 | 5 | 5 |
| 89 | 20 | 1 | 3 | 5 |
|  | 100 | 4 | 4 | 5 |
| 90 | 20 | 5 | 5 | 5 |
|  | 100 | 5 | 5 | 5 |

X: *Ortyza sativa* L.
Y: *Echinochloa crus-galli* L.
A: *Raphanus sativus* L.

What we claim is:
1. A compound of the formula:

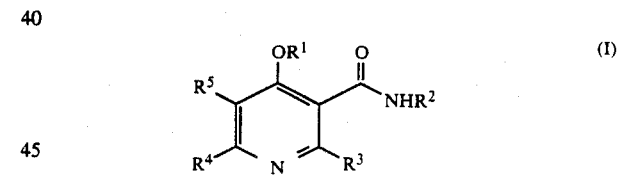

wherein
R$^1$ is C$_1$–C$_8$ alkyl, C$_2$–C$_6$ alkenyl, C$_2$–C$_6$ alkynyl, aralkyl selected from the group consisting of benzyl, 2-phenylethyl, 3-phenylpropyl and 4-phenylbutyl, haloalkyl, C$_1$–C$_6$ alkoxy-C$_1$–C$_6$ alkyl, C$_1$–C$_6$ alkylthio-C$_1$–C$_6$ alkyl or C$_1$–C$_6$ alkoxycarbonyl-C$_1$–C$_6$ alkyl;

R$^2$ is unsubstituted or substituted phenyl or naphthyl, wherein the substituents are selected from the group consisting of halogen, C$_1$–C$_6$ alkyl, C$_1$–C$_6$ alkoxy, C$_1$–C$_6$ alkoxycarbonyl, trifluoromethyl, cyano or nitro;

R$_3$ and R$_4$ are selected from the group consisting of C$_1$–C$_6$ alkyl, aralkyl selected from the group consisting of benzyl, 2-phenylethyl, 3-phenylpropyl and 4-phenylbutyl, haloalkyl, C$_3$–C$_6$ cycloalkyl, unsubstituted phenyl or naphthyl, and substituted phenyl or naphthyl, wherein the substituents are selected form the group consisting of halogen, C$_1$–C$_6$ alkyl, C$_1$–C$_6$ alkoxy, trifluoromethyl, cyano or nitro;

$R^5$ is hydrogen, halogen, $C_1$–$C_6$ alkyl, or unsubstituted or substituted phenyl or aralkyl selected from the group consisting of benzyl, 2-phenylethyl, 3-phenylpropyl and 4-phenylbutyl, wherein the substituents are selected from the group consisting of halogen, $C_1$–$C_6$ alkyl, $C_1$–$C_6$ alkoxy, trifluoromethyl, cyano or nitro;

$R^4$ and $R^5$ or a 1-oxide or an acid addition salt thereof.

2. A compound of claim 1 in which $R^2$ is 2,6-diethylphenyl group.

3. A compound of claim 1 in which $R^2$ is 2,3-dimethylphenyl group.

4. A compound of claim 1 which is 2,6-dimethyl-N-(2,3-dimethylphenyl)-4-propoxy-3-pyridinecarboxamide, 4-butoxy-2,6-dimethyl-N-(2,3-dimethylphenyl)-3-pyridinecarboxamide, 4-isobutoxy-2,6-dimethyl-N-(2,3-dimethylphenyl)-3-pyridinecarboxamide, 2,6-dimethyl-N-(2,3-dimethylphenyl)-4-pentyloxy-3-pyridinecarboxamide, 4-isopentyloxy-2,6-dimethyl-N-(2,3-dimethylphenyl)-3-pyridinecarboxamide, 4-allyloxy-2,6-dimethyl-N-(2,3-dimethylphenyl)-3-pyridinecarboxamide, N-(2,6-diethylphenyl)-2,6-dimethyl-4-propoxy-3-pyridinecarboxamide, N-(2,6-diethylphenyl)-4-isopropoxy-2,6-dimethyl-3-pyridinecarboxamide, 4-butoxy-N-(2,6-diethylphenyl)-2,6-dimethyl-3-pyridinecarboxamide, N-(2,6-diethylphenyl)-4-isobutoxy-2,6-dimethyl-3-pyridinecarboxamide, N-(2,6-diethylphenyl)-2,6-dimethyl-4-pentyloxy-3-pyridinecarboxamide, 5-bromo-N-(2,6-diethylphenyl)-2,6-dimethyl-4-propoxy-3-pyridinecarboxamide, 6-methyl-N-(2,3-dimethylphenyl)-2-phenyl-4-propoxy-3-pyridinecarboxamide, N-(2,6-diethylphenyl)-6-methyl-2-phenyl-4-propoxy-3-pyridinecarboxamide, 5-bromo-N-(4-bromo-2,6-diethylphenyl)-2,6-dimethyl-4-propoxy-3-pyridinecarboxamide, 2-ethyl-N-(2,6-diethylphenyl)-6-methyl-4-propoxy-3-pyridinecarboxamide, N-(2,6-diethylphenyl)-2,5,6-trimethyl-4-propoxy-3-pyridinecarboxamide, 2,6-diethyl-N-(2,6-diethylphenyl)-4-propoxy-3-pyridinecarboxamide, or N-(2,6-diethylphenyl)-4-isobutoxy-5,6-dimethyl-2-propyl-3-pyridinecarboxamide, or their respective 1-oxides or addition salts.

* * * * *